(12) United States Patent
Summers et al.

(10) Patent No.: US 7,260,250 B2
(45) Date of Patent: Aug. 21, 2007

(54) COMPUTER-AIDED CLASSIFICATION OF ANOMALIES IN ANATOMICAL STRUCTURES

(75) Inventors: Ronald M. Summers, Potomac, MD (US); Marek Franaszek, Gaithersburg, MD (US); Gheorghe Iordanescu, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 872 days.

(21) Appl. No.: 10/671,749

(22) Filed: Sep. 26, 2003

(65) Prior Publication Data

US 2004/0064029 A1 Apr. 1, 2004

Related U.S. Application Data

(60) Provisional application No. 60/415,308, filed on Sep. 30, 2002.

(51) Int. Cl.
*G06K 9/00* (2006.01)
(52) U.S. Cl. ...................................... 382/128; 382/286
(58) Field of Classification Search ................ 382/128, 382/131, 199, 173, 159, 224; 600/416
See application file for complete search history.

(56) References Cited

U.S. PATENT DOCUMENTS

| | | | |
|---|---|---|---|
| 4,569,014 A | 2/1986 | Kishi et al. | |
| 4,710,876 A | 12/1987 | Cline et al. | |
| 4,719,585 A | 1/1988 | Cline et al. | |
| 4,729,098 A | 3/1988 | Cline et al. | |
| 4,745,562 A | 5/1988 | Prazdny | |
| 4,751,643 A | 6/1988 | Lorensen et al. | |
| 4,791,567 A | 12/1988 | Cline et al. | |
| 4,821,210 A | 4/1989 | Rumbaugh | |
| 4,821,213 A | 4/1989 | Cline et al. | |
| 4,831,528 A | 5/1989 | Crawford et al. | |
| 4,868,748 A | 9/1989 | Crawford et al. | |

(Continued)

FOREIGN PATENT DOCUMENTS

JP 07332970 12/1995

(Continued)

OTHER PUBLICATIONS

"Stereo Matching with Transparency and Matting," CVPR '97, pp. 1-8, submitted Jun. 17-19, 1997.

(Continued)

*Primary Examiner*—Andrew W. Johns
*Assistant Examiner*—Claire Wang
(74) *Attorney, Agent, or Firm*—Klarquist Sparkman, LLP

(57) ABSTRACT

Candidate anomalies in an anatomical structure are processed for classification. For example, false positives can be reduced by techniques related to the anomaly's neck, wall thickness associated with the anomaly, template matching performed for the anomaly, or some combination thereof. The various techniques can be combined for use in a classifier, which can determine whether the anomaly is of interest. For example, a computed tomography scan of a colon can be analyzed to determine whether a candidate anomaly is a polyp. The technologies can be applied to a variety of other scenarios involving other anatomical structures.

44 Claims, 16 Drawing Sheets

U.S. PATENT DOCUMENTS

| | | | |
|---|---|---|---|
| 4,879,668 A | 11/1989 | Cline et al. |
| 4,882,679 A | 11/1989 | Tuy et al. |
| 4,896,278 A | 1/1990 | Grove |
| 4,903,202 A | 2/1990 | Crawford |
| 4,905,148 A | 2/1990 | Crawford |
| 4,914,589 A | 4/1990 | Crawford |
| 4,953,087 A | 8/1990 | Crawford |
| 4,984,157 A | 1/1991 | Cline et al. |
| 4,985,834 A | 1/1991 | Cline et al. |
| 4,985,856 A | 1/1991 | Kaufman |
| 4,987,554 A | 1/1991 | Kaufman |
| 4,989,142 A | 1/1991 | Crawford |
| 4,991,092 A | 2/1991 | Greensite |
| 4,999,789 A | 3/1991 | Fiasconaro |
| 5,016,173 A | 5/1991 | Kenet et al. |
| 5,038,302 A | 8/1991 | Kaufman |
| 5,068,788 A | 11/1991 | Goodenough et al. |
| 5,095,521 A | 3/1992 | Trousset et al. |
| 5,101,475 A | 3/1992 | Kaufman |
| 5,113,357 A | 5/1992 | Johnson et al. |
| 5,133,020 A | 7/1992 | Giger et al. |
| 5,150,427 A | 9/1992 | Frazee et al. |
| 5,166,876 A | 11/1992 | Cline et al. |
| 5,170,347 A | 12/1992 | Tuy et al. |
| 5,179,441 A | 1/1993 | Anderson et al. |
| 5,187,658 A | 2/1993 | Cline et al. |
| 5,257,203 A | 10/1993 | Riley et al. |
| 5,268,967 A | 12/1993 | Jang et al. |
| 5,273,040 A | 12/1993 | Apicella et al. |
| 5,277,182 A | 1/1994 | Koizumi et al. |
| 5,289,374 A | 2/1994 | Doi et al. |
| 5,291,402 A | 3/1994 | Pfoh |
| 5,297,550 A | 3/1994 | Margosian |
| 5,309,356 A | 5/1994 | Nishide et al. |
| 5,319,549 A | 6/1994 | Katsuragawa et al. |
| 5,319,551 A | 6/1994 | Sekiguchi et al. |
| 5,345,490 A | 9/1994 | Finnigan et al. |
| 5,361,763 A | 11/1994 | Kao et al. |
| 5,371,778 A | 12/1994 | Yanof et al. |
| 5,381,518 A | 1/1995 | Drebin et al. |
| 5,412,763 A | 5/1995 | Knoplioch et al. |
| 5,425,368 A | 6/1995 | Brandt |
| 5,442,733 A | 8/1995 | Kaufman et al. |
| 5,452,367 A | 9/1995 | Bick et al. |
| 5,458,111 A | 10/1995 | Coin |
| 5,465,323 A | 11/1995 | Mallet |
| 5,489,782 A | 2/1996 | Wernikoff |
| 5,499,322 A | 3/1996 | Thirion et al. |
| 5,506,785 A | 4/1996 | Blank et al. |
| 5,517,602 A | 5/1996 | Natarajan |
| 5,531,227 A | 7/1996 | Schneider |
| 5,537,485 A | 7/1996 | Nishikawa et al. |
| 5,550,376 A | 8/1996 | Gupta et al. |
| 5,553,207 A | 9/1996 | Sekiguchi et al. |
| 5,555,352 A | 9/1996 | Lucas |
| 5,559,847 A | 9/1996 | Hu et al. |
| 5,574,763 A | 11/1996 | Dehner |
| 5,582,173 A | 12/1996 | Li |
| 5,604,778 A | 2/1997 | Polacin et al. |
| 5,611,000 A | 3/1997 | Szeliski et al. |
| 5,611,025 A | 3/1997 | Lorensen et al. |
| 5,623,586 A | 4/1997 | Hohne |
| 5,627,907 A | 5/1997 | Gur et al. |
| 5,630,034 A | 5/1997 | Oikawa et al. |
| 5,636,338 A | 6/1997 | Moreton |
| 5,699,799 A | 12/1997 | Xu et al. |
| 5,719,954 A | 2/1998 | Onda |
| 5,734,384 A | 3/1998 | Yanof et al. |
| 5,782,762 A | 7/1998 | Vining |
| 5,920,319 A | 7/1999 | Vining et al. |
| 5,936,628 A | 8/1999 | Kitamura et al. |
| 5,971,767 A | 10/1999 | Kaufman et al. |
| 5,986,662 A | 11/1999 | Arigiro et al. |
| 6,078,680 A | 6/2000 | Yoshida et al. |
| 6,125,194 A | 9/2000 | Yeh et al. |
| 6,130,671 A | 10/2000 | Argiro |
| 6,219,059 B1 | 4/2001 | Argiro |
| 6,246,784 B1 | 6/2001 | Summers et al. |
| 6,272,366 B1 | 8/2001 | Vining |
| 6,331,116 B1 | 12/2001 | Kaufman et al. |
| 6,343,936 B1 | 2/2002 | Kaufman et al. |
| 6,345,112 B1 | 2/2002 | Summers et al. |
| 2001/0044576 A1* | 11/2001 | Vining ........................ 600/416 |
| 2002/0164061 A1* | 11/2002 | Paik et al. .................. 382/131 |
| 2004/0165767 A1* | 8/2004 | Gokturk et al. ............. 382/159 |
| 2005/0163356 A1* | 7/2005 | Makram-Ebeid et al. ... 382/128 |

FOREIGN PATENT DOCUMENTS

| | | |
|---|---|---|
| WO | WO96/13207 | 5/1996 |
| WO | WO98/11524 | 3/1998 |
| WO | WO98/37517 | 8/1998 |
| WO | WO 00/55812 | 9/2000 |
| WO | WO 00/55814 | 9/2000 |

OTHER PUBLICATIONS

"E-Z-EM Debuts Virtual Colonoscopy Tagging Agent," http://www.auntminnie.com/print/print.asp?sec=rca&sub=rsna_2001&pag=dis&ItemId=52233, Nov. 26, 2001.

Arimura et al., "Performance Evaluation of an Advanced Method for Automated Identification of View Positions of Chest Radiographs by Use of a Large Database," *Proceedings of SPIE*, vol. 4684, pp. 308-315, Paper #4684-32, Feb. 2002. (Abstract Only).

Ashton et al., "A Novel Volumetric Feature Extraction Technique, with Applications to MR Images," *IEEE*, pp. 564-567, Sep. 1995.

Barnes, "New CAD Technique Improves CT Colonography," http://www.auntminnie.com/print/print.asp?sec=sup&sub=cto&pag=dis&ItemId=52410&print, Dec. 21, 2001.

Barnes, "CT Colonography Performs Very Well in Five-Year Study," http://www.auntminnie.com/print/print.asp?sec=sup&sub=cto&pag=dis&ItemId=52240&print, Nov. 26, 2001.

Besl et al., "Segmentation Through Variable-Order Surface Fitting," *IEEE Transactions on Pattern Analysis and Machine Intelligence*, vol. 10, No. 2, pp. 167-192, Mar. 1988.

Besl, *Surfaces in Range Image Understanding*, Springer-Verlag New York Inc., pp. 63-115 and 157-160, 1988.

Cai et al., "Displaying of Details in Subvoxel Accuracy," *Journal of Computer Science and Technology*, vol. 11, No. 5, pp. 480-488, Sep. 1996. (Abstract Only).

Chen et al., "A Novel Approach to Extract Colon Lumen from CT Images for Virtual Colonoscopy," *IEEE Transactions on Medical Imaging*, vol. 19, No. 12, Dec. 2000.

Chiou et al., "Interactive Path Planning for Virtual Endoscopy," *Conf Record IEEE NSS-MIC*, Nov. 1998.

Chiou et al., "Volume Segmentation and Rendering of Mixtures of Materials for Virtual Colonoscopy," *SPIE Medicial Imaging '99*, vol. 3660, pp. 133-138, Feb. 1999.

Chiou et al., "Unified Analysis, Modeling, Matching and Synthesis for CT Color Texture Mapping from the Visible Human Dataset," *The Second Visible Human COnf.*, Bethesda, MD, Oct. 1998.

Cline et al., "Three-Dimensional Segmentation of MR Images of the Head Using Probability and Connectivity," *Journal of Computer Assisted Tomography*, vol. 14, No. 6, pp. 1037-1045, Nov.-Dec. 1990.

Davatzikos et al., "Using a Deformable Surface Model to Obtain a Shape Representation of the Cortex," *IEEE Transactions on Medical Imaging*, vol. 15, No. 6, pp. 785-795, Dec. 1996.

Dill, "An Application of Color Graphics to the Display of Surface Curvature," *Computer Graphics*, vol. 15, No. 3, pp. 153-161, Aug. 1981.

Fielding et al., "Tumor Detection by Virtual Cystoscopy with Color Mapping of Bladder Wall Thickness," *The Journal of Urology*, vol. 167, pp. 559-562, Feb. 2002.

Fielding et al., "CT Cystoscopy: Comparision of Axial Source Images with Color Wall Mapping for Identification of Bladder Tumors," *Radiology*, vol. 221(P), Presentation 1228, 2001. (Abstract Only).

Guo et al., "A New Method for Computer Recognition of Small Rounded Pneumoconiosis Opacities in Chest X-Rays," Eighth International Conference on Pattern Recognition, *IEEE Computer Society Press*, pp. 475-477, 1986.

He et al., "Fast Stereo Volume Rendering," *IEEE*, pp. 49-56 and 466, 1996.

Hong et al., "3D Reconstruction and Visualization of the Inner Surface of the Colon from Spiral CT Data," *IEEE*, pp. 1506-1510, 1997.

Ichimura, "Volume Data Coding Based on Region Segmentation Using Finite Mixture Model," *Proceedings of 3rd IEEE International Conference on Image Processing*, Sep. 16-19, 1996.

Kawaguchi et al., "Virtual Cystocopy of Urinary Bladder Using Multirow Detector CT: Assessment of Clinical Utility," *Radiology*, vol. 221(P), Presentation 1229, 2001. (Abstract Only).

Kawata et al., "An Approach for Detecting Blood Vessel Diseases from Cone-Beam CT Image," *In Proc. of ICIP-95*, vol. 2, pp. 500-503, Oct. 23-26, 1995.

Kawata et al., "Feature Extraction of Convex Surfaces on Blood Vessels Using Cone-Beam CT Images," International Conference on Image Processing, *IEEE*, vol. 3, pp. 315-318, Sep. 1996.

Kawata et al., "Measurement of Blood Vessel Characteristics for Disease Detection Based on Cone-Beam CT Images," *IEEE Transactions on Nuclear Science*, vol. 43, No. 6, pp. 3348-3354, Part 2, Dec. 1996. (Abstract only).

Lacrosse et al., "3D Spiral CT of the Tracheobronchial Tree," *Journal of Computer Assisted Tomography*, vol. 19, No. 3, pp. 341-347, May-Jun. 1995.

Lee et al., "Automated Detection of Pulmonary Nodules in Helical CT Images Based on an Improved Template-Matching Technique," *IEEE Transactions on Medical Imaging*, vol. 20, No. 7, pp. 595-604, Jul. 2001.

Liang et al., "Inclusion of a *Priori* Information in Segmentation of Colon Lumen for 3D Virtual Colonoscopy," *IEEE Nuclear Science Symposium Conference Record*, vol. 2, pp. 1423-1427, 1997.

Liang, "Virtual Colonoscopy: An Alternative Approach to Examination of the Entire Colon," http://www.viatronix.net/white_paper_pdfs/LIT1012.pdf, visited Aug. 1, 2002.

Lorensen et al., "The Exploration of Cross-Sectional Data with a Virtual Endoscope," *Interactive Technology and the New Health Paradigm*, IOS Press, pp. 221-230, Jan. 1995.

Lorensen, et al., Marching Cubes: A High Resolution 3D Surface Construction Algorithm, *Computer Graphics*, vol. 21, No. 4, pp. 163-169, 1987.

Mergo et al., "Three-dimensional CT of the Tracheobronchial Tree: Correlative Study with Bronchoscopy in 30 Cases," *Scientific Sessions*, p. 261. (Abstract only).

Monga et al., "Using Partial Derivatives of 3D Images to Extract Typical Surface Features," *Computer Vision and Image Understanding*, vol. 61, No. 2, pp. 171-189, Mar. 1995.

Näppi et al., "Automated Detection of Polyps with CT Colonography: Evaluation of Volumetric Features for Reduction of False-Positive Findings," *Academic Radiology*, vol. 9, No. 4, pp. 386-397, Apr. 2002.

Rogers et al., *Mathematical Elements for Computer Graphics*, McGraw-Hill Publishing Co., New York, 2nd Ed., pp. 420-421, 1990.

Röll et al., "Fast Generation of Leakproof Surfaces from Well-Defined Objects by a Modified Marching Cubes Algorithm," *Computer Graphics Forum*, vol. 14, No. 2, pp. 127-138, 1995.

Sandor et al., "Segmentation of Brain CT Images Using the Concept of Region Growing," *Int J. Biomed. Comput.*, vol. 29, pp. 133-140, 142, 146-147, 1991.

Scharstein et al., "Stereo Matching with Non-Linear Diffusion," *Proceedings of the 1996 IEEE Computer Society Conference on Computer Vision and Pattern Recognition*, pp. 343-350, Jun. 18-20, 1996.

Scharstein, "Stereo Vision for View Synthesis," *Proceedings of the IEEE Conference on Computer Vision and Pattern Recognition*, 1996, pp. 852-858, Jun. 18-20, 1996.

Schreyer et al., "Virtual CT Cystoscopy: Color Mapping of Bladder Wall Thickness," *Investigative Radiology*, vol. 35, No. 5, pp. 331-334, 2000.

Sekiguchi et al., "Interactive 3-Dimensional Segmentation Method Based on Region Growing Method," *Systems and Computers in Japan*, vol. 25, No. 1, pp. 88-97, 1994.

Sonka et al., "Rule-Based Detection of Intrathoracic Airway Trees," *IEEE Transactions on Medical Imaging*, vol. 15, No. 3, pp. 314-326, Jun. 1996.

Stringham et al., "Probabilistic Segmentation Using Edge Detection and Region Growing," *Visualization in Biomedical Computing*, SPIE vol. 1808, pp. 40-51, 1992.

Summers et al., "CT Virtual Bronchoscopy of Simulated Endobronchial Lesions: Effect of Scanning, Reconstruction, and Display Settings and Potential Pitfalls," *AJR*, vol. 170, pp. 947-950, Apr. 1998.

Summers, "Image Gallery: A Tool for Rapid Endobronchial Lesion Detection and Display Using Virtual Bronchoscopy," *Journal of Digital Imaging*, vol. 11, No. 3, Supplement 1, pp. 53-55, Aug. 1998.

Summers et al., "Automatic Detection of Endobronchial Lesions with Virtual Bronchoscopy: Comparison of Two Methods," *Proceedings of SPIE Reprint: Reprinted from Medical Imaging 1998: Image Processing*, vol. 3338, pp. 327-335, Feb. 23-26, 1998.

Summers et al., "Automated Polyp Detector for CT Colonography: Feasibility Study," *Radiology*, 216:284-290, 2000.

Summers, "Navigational Aids for Real-Time Virtual Bronchoscopy," *AJR*, vol. 168, pp. 1165-1170, May 1997.

Summers et al., "Polypoid Lesions of Airways: Early Experience with Computer-assisted Detection by Using Virtual Bronchoscopy and Surface Curvature," *Radiology*, vol. 208, No. 2, pp. 331-337, Aug. 1998.

Summers et al., "Virtual Bronchoscopy: Segmentation Method for Real-Time Display," *Radiology*, vol. 200, No. 3, pp. 857-862, Sep. 1996.

Summers et al., "Computer-Assisted Detection of Endobronchial Lesions Using Virtual Bronchoscopy: Application of Concepts From Differential Geometry," May 27, 1997. (Abstract only).

Taubin, "A Signal Processing Approach to Fair Surface Design," *Computer Graphics Proceedings*, SIGGRAPH 95, pp. 351-358, Aug. 6-11, 1995.

Thirion et al., "Computing the Differential Characteristics of Isointensity Surfaces," *Computer Vision and Image Understanding*, vol. 61, No. 2, pp. 190-202, Mar. 1995.

Udupa, "Interactive Segmentation and Boundary Surface Formation for 3-D Digital Images," *Computer Graphics and Image Processing*, vol. 18, pp. 213-235, 1982.

Van Gelder et al., "Direct Volume Rendering with Shading via Three-Dimensional Textures," *Proceedings 1996 Symposium on Volume Visualization*, pp. 23-30, 1996.

Vining et al., "Virtual Bronchoscopy: Relationships of Virtual Reality Endobronchial Simulations to Actual Bronchoscopic Findings," *Chest*, vol. 109, No. 2, pp. 549-553, Feb. 1996.

Vining et al., "Virtual Colonoscopy," *Radiology*, 193(P):446, 1994.

Vining et al., "Virtual Bronchoscopy," *Radiology*, 193(P):261, 1994.

Vos et al., "A New Visualization Method for Virtual Colonoscopy," *Medical Image Computing and Computer-Assisted Intervention—MICCAI2001* (W.J. Niessen and A. Viergever, eds.), Springer-Verlag, pp. 645-654, Oct. 2001.

Vos et al., "A Review of Technical Advances in Virtual Colonoscopy," *MEDINFO 2001, Proc. 10th World Congress on Medical Informatics* (London, Sep. 2-5, 2001), V. Patel et al. (Eds.), Amsterdam: IOS Press, vol. 2, pp. 938-942, 2001.

Wax et al., "Electronic Colon Cleansing for Virtual Colonoscopy," Department of Radiology and Computer Science, State University of New York at Stony Brook, *1st Intl. Conference on Virtual Colonoscopy*, Boston, MA, 1998.

Wiesner, et al., "Normal Colonic Wall Thickness at CT and Its Relation to Colonic Distension," *Radiology*, vol. 221(P), Presentation 1088, 2001. (Abstract Only).

Wood et al., "Measurement of Three-Dimensional Lung Tree Structures by Using Computed Tomography," *American Physiological Society*, pp. 1687-1697, 1995.

Wood et al., "A Method for Measurement of Cross Sectional Area, Segment Length, and Branching Angle of Airway Tree Structures in Situ," *Computerized Medical Imaging and Graphics*, vol. 19, No. 1, pp. 145-150, 151-152, 1995.

Zhou et al., "Three-Dimensional Skeleton and Centerline Generation Based on an Approximate Minimum Distance Field," *The Visual Computer*, vol. 14, pp. 303-314, 1998.

Burgard et al., "Active Mobile Robot Localization by Entrophy Minimization," Proceedings Second Euromicro Workshop on Advanced Mobile Robots, pp. 155-162, 1997.

Chen et al., "A Fast Algorithm to Generate Centerline for Virtual Colonoscopy," SPIE Conference, 2 pages, Feb. 18-20, 2000.

Chen et al., "A Tree-Branch Searching, Multiresolution Approach to Skeletonization for Virtual Endoscopy," Proc SPIE Medical Imaging, 9 pages, 2000.

Chen et al., "MRI-Based Virtual Cystoscopy: The Image Segmentation and Visualization," SPIE Conference, 2 pages, Feb. 18-20, 2000.

Chen et al., "Virtual Laryngoscopy: Feasibility Studies by CT and MRI," IEEE Medical Imaging Conference, 6 pages, Nov. 1999.

Hagen et al., "Methods for Surface Interrogation," Proceedings of the Conference on Visualization, vol. CONF 1, pp. 187-193, 1990.

Holzapfel et al., "Large Strain Analysis of Soft Biological Membranes: Formulation and Finite Element Analysis," Computer Methods in Applied Mechanics and Engineering, vol. 132, No. 1-2, pp. 45-61, 1996.

Hong et al., "3D Virtual Colonoscopy," 1995 Biomedical Visualization Proceedings, 7 pages, 1995.

Kaufman et al., "Disobstruction of Colon Wall Collapse," Project Description, online www.cs.sunysc.edu, 1 page, Jan. 1999.

Kaye et al., "A 3D Virtual Environment for Modeling Mechanical Cardiopulmonary Interactions," CVRMED-MRCA '97, pp. 389-398, 1997.

Pai et al., "Multiresolution Rough Terrain Motion Planning," IEEE Transactions on Robotics and Automatic, vol. 14, No. 1, pp. 19-33, 1998.

Penenberg, "From Stony Brook, a New Way to Examine Colons, Externally," The New York Times, p. 6, Apr. 14, 1996.

Robb, "Virtual (Computed) Endoscopy: Development and Evaluation Using the Visible Human Datasets," http://www.mayo.edu/bir/nlmpaper/robb_pap.htm, Mayo Foundation/Clinic, 28 pages, Presented at the Visible Human Project Conference, Oct. 7-8, 1996.

Shibolet et al., "Coloring Voxel-Based Objects for Virtual Endoscopy," IEEE Symposium on Volume Visualization, Research Triangle, pp. 15-22, Oct. 1998.

Valev et al., "Techniques of CT Colonography (Virtual Colonoscopy)," Critical Reviews in Biomedical Engineering, Begall House, vol. 27, No. 1-2, pp. 1-25, 1999.

You et al., "Interactive Volume Rendering for Virtual Colonoscopy," Proceedings Visualization '97, pp. 443-446, 1997.

\* cited by examiner

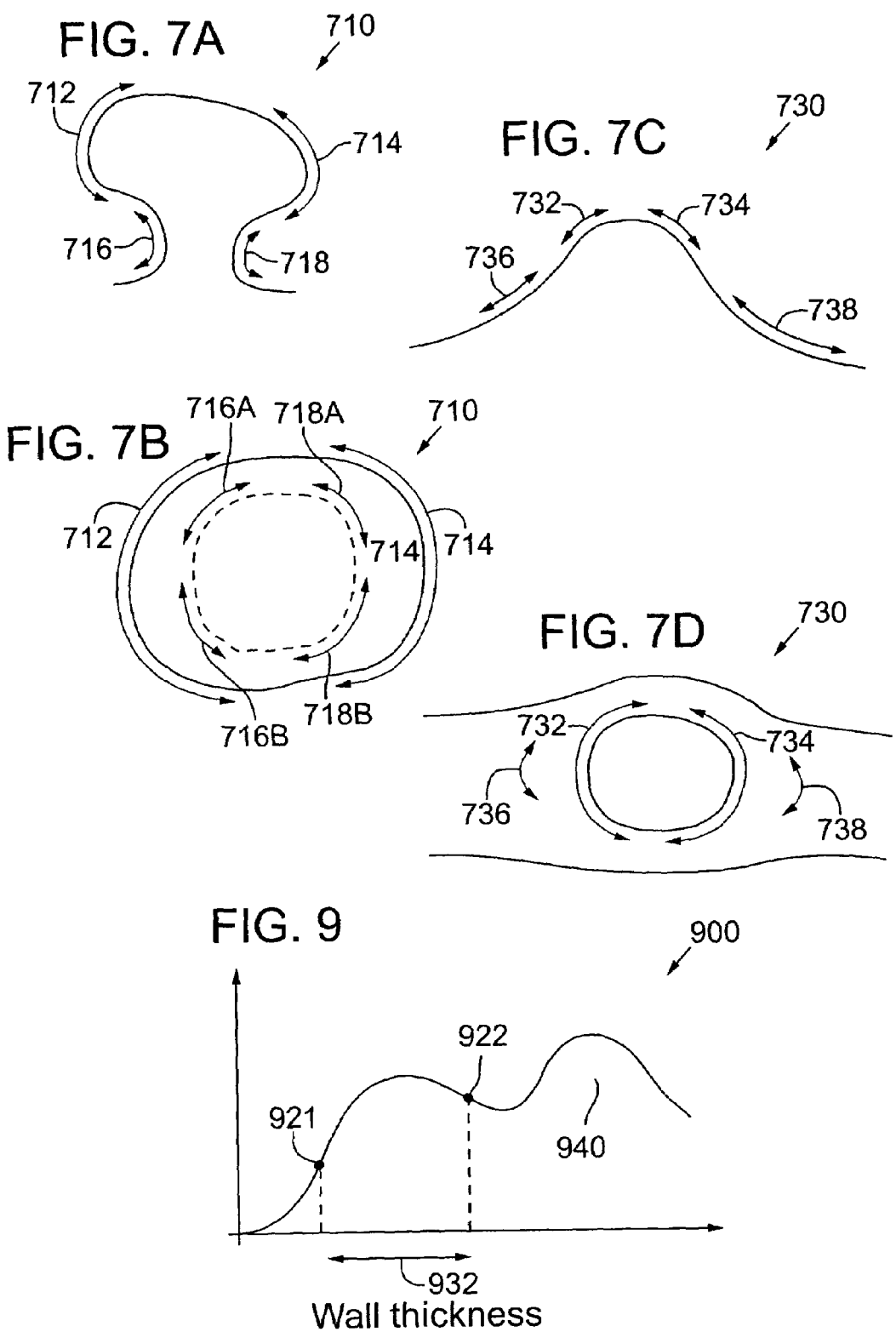

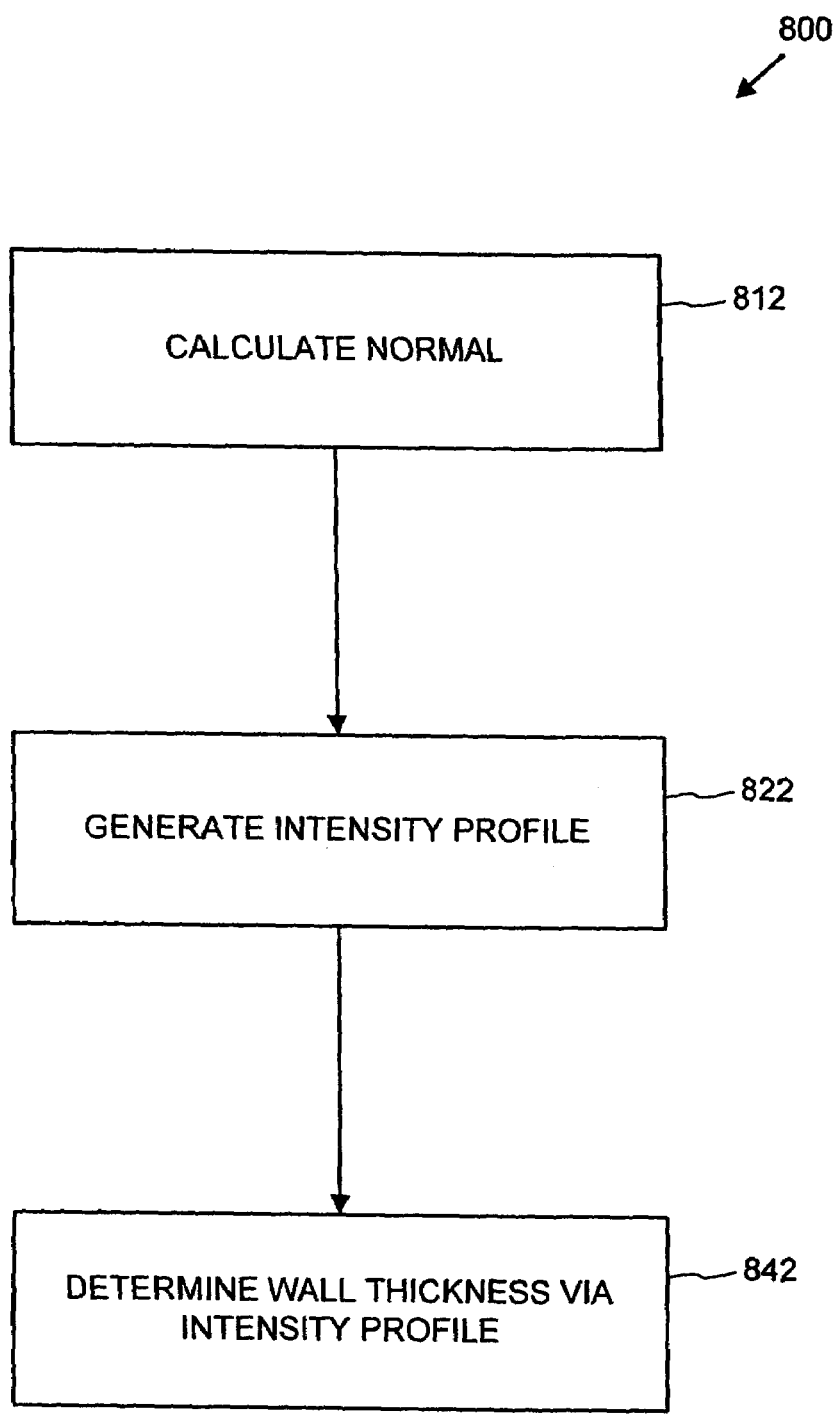

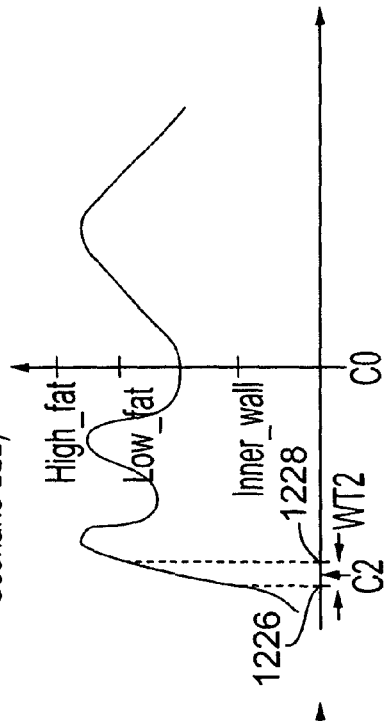
FIG. 12A Scenario I)
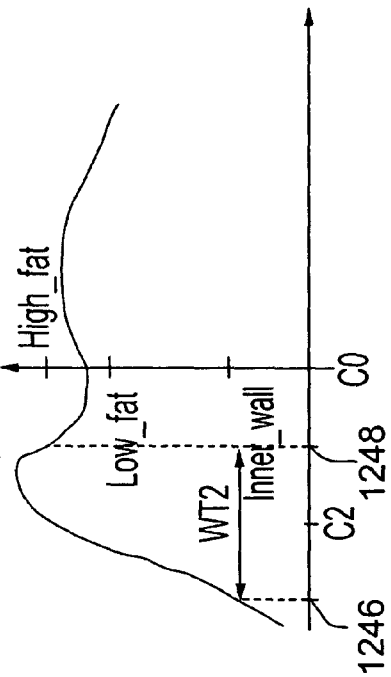
FIG. 12B Scenario III)
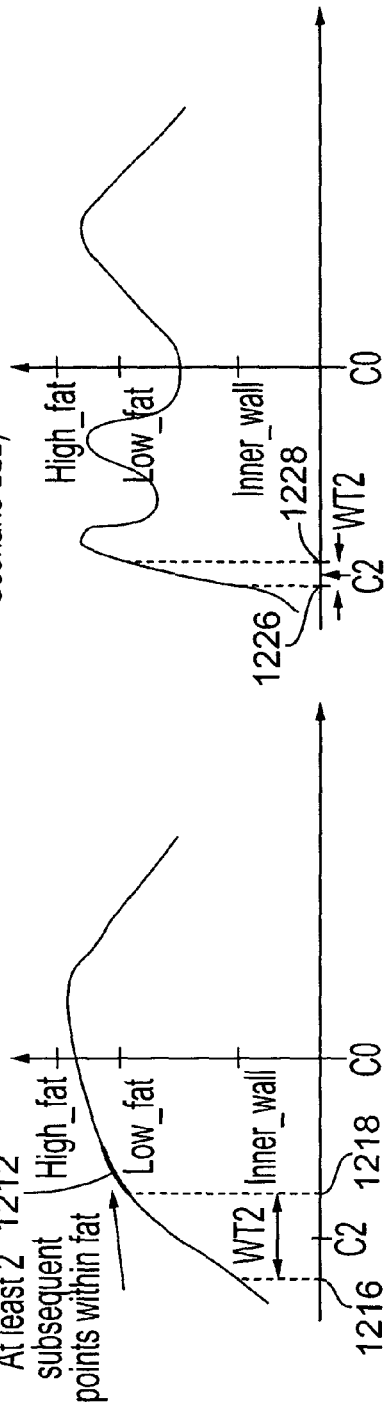
FIG. 12C pure case Scenario II)A
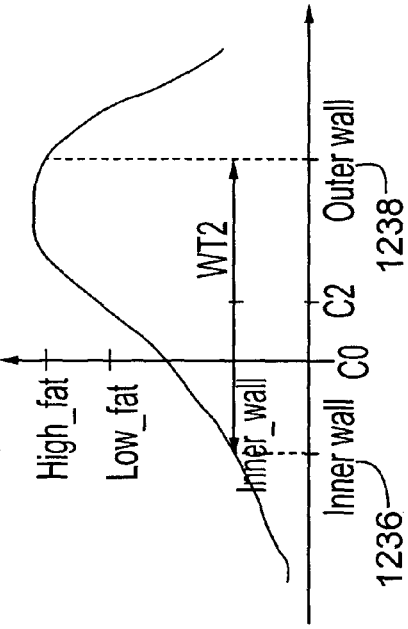
FIG. 12D Indirect case Scenario II)B

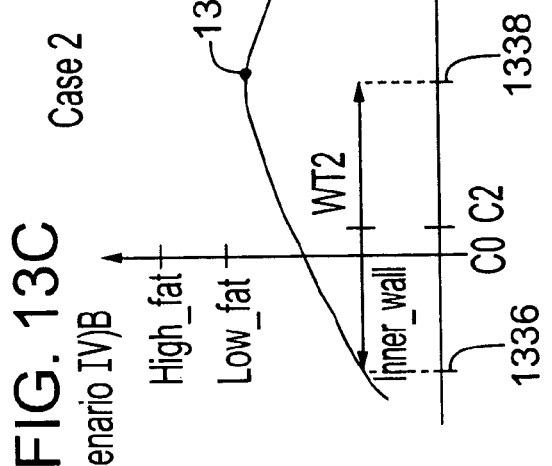
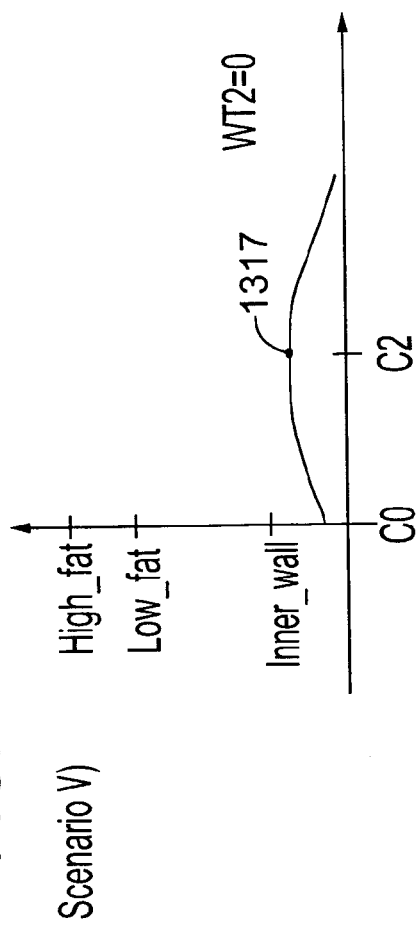
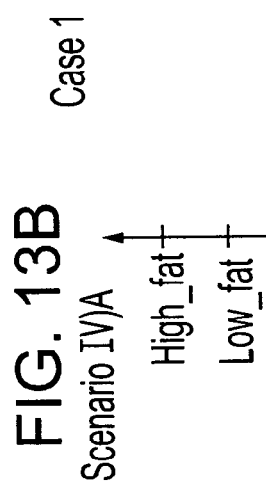
FIG. 13A Scenario V)
FIG. 13B Scenario IV)A Case 1
FIG. 13C Scenario IV)B Case 2

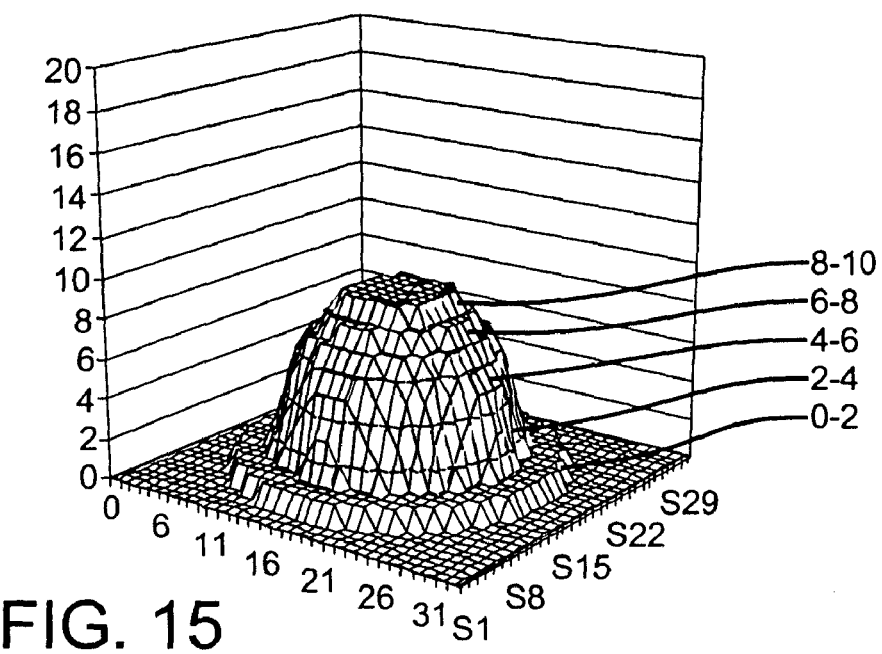
FIG. 15
FIG. 16
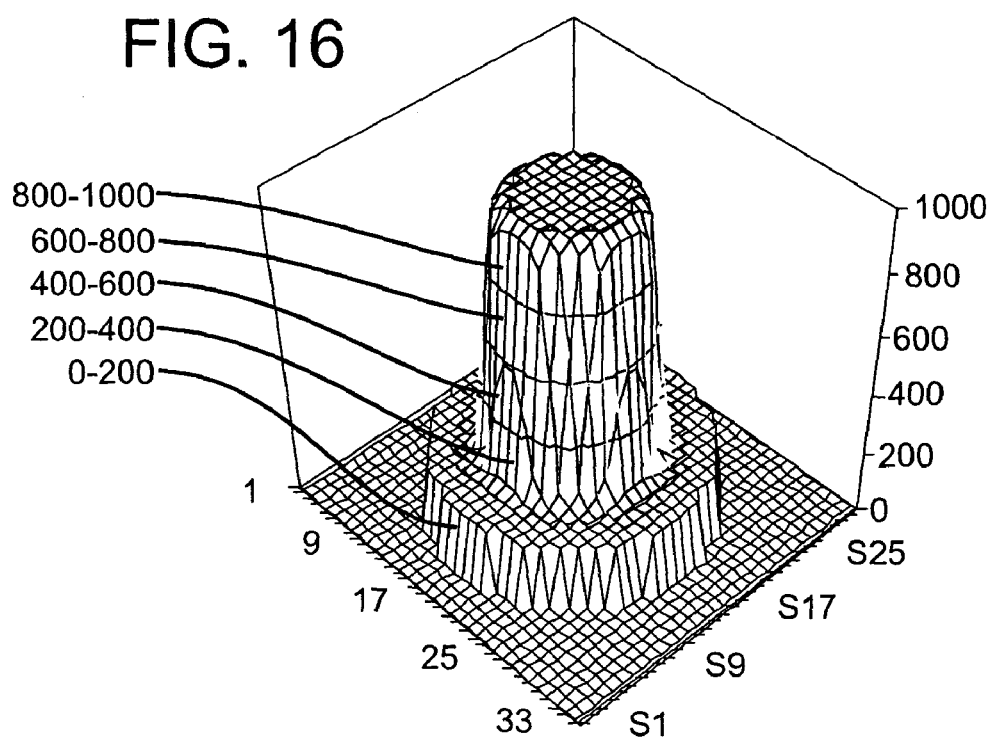

COMPUTER-AIDED CLASSIFICATION OF ANOMALIES IN ANATOMICAL STRUCTURES

CROSS-REFERENCE TO RELATED APPLICATION

This application claims the benefit of U.S. Provisional Patent Application No. 60/415,308, filed Sep. 30, 2002, by Summers et al., entitled "COMPUTER-AIDED CLASSIFICATION OF ANOMALIES IN ANATOMICAL STRUCTURES," which is hereby incorporated by reference.

FIELD

The field relates to automated analysis of digital representations of anatomical structures.

BACKGROUND

Due to the availability of technology for non-invasive observation of soft tissues of the human body, significant advances have been made in the field of medicine. For example, a number of machines now make it possible to routinely observe anatomical structures such as the heart, colon, bronchus, and esophagus.

Due to widespread availability of skilled technicians and reduction in cost of the necessary equipment, non-invasive observations can now be employed as a part of routine preventive medicine via periodic examinations. The availability of such non-invasive capabilities both reduces the risk of observation-related injury or complication and reduces discomfort and inconvenience for the observed patient. As a result, patients tend to allow observation to be done more frequently, and medical conditions requiring attention can be detected early. For example, anomalies in an anatomical structure can be identified and diagnosed at an early stage, when treatment is more likely to be successful.

In one popular observation technique called "Computed Tomography Imaging" ("CT Scan"), multiple two-dimensional image slices are taken of a particular section of the patient's body. A physician can then analyze the slices to detect any anomalies within the observed section. Out of the anomalies found, the physician can judge which are anomalies of interest requiring further attention or treatment.

To assure adequate coverage of the section being observed, a large number of slices can be obtained to increase the observation resolution. However, as the number of slices increases, the amount of data presented to the physician becomes overwhelming. Accordingly, various software technologies have been applied with some success to aid the physician in analyzing the data to find anomalies.

Although progress has been made in employing software to assist in detection of anomalies in anatomical structures, there are significant limitations to the current techniques. For example, one problem consistently plaguing such systems is the overabundance of false positives.

Typically, the software approach correctly identifies anomalies of interest (i.e., the software exhibits superior sensitivity). However, the software also tends to incorrectly identify too many anomalies as anomalies of interest (i.e., the software exhibits poor selectivity). An anomaly incorrectly identified as an anomaly of interest is sometimes called a "false positive."

False positives are troublesome because any identified positives must be considered and evaluated by a human classifier (e.g., the physician). Even if the physician can quickly dismiss an anomaly as a false positive, too many false positives consume an inordinate amount of time and limit the usefulness of the software-based approach.

There thus remains a need for a way to improve the computer-based approaches for identifying anomalies of interest in anatomical structures. For example, selectivity can be improved.

SUMMARY

Embodiments described herein include methods and systems for analyzing a digital representation of an anatomical structure to classify anomalies in the anatomical structure. For example, an anomaly can be classified as of interest (e.g., a likely polyp or lesion requiring further evaluation and consideration) or not of interest (e.g., an anomaly such as a false positive or a misidentified normal feature that does not require further evaluation).

In some embodiments, a set of one or more candidate anomalies is processed via a number of techniques to collect various characteristics of the anomalies. A software classifier can use the characteristics to classify an anomaly in the set (e.g., as of interest or not of interest).

In some embodiments, the neck of an anomaly can be identified. The neck can then be analyzed to collect a set of one or more neck characteristics. Based on the neck characteristics, a software classifier can make a more accurate classification.

In some embodiments, the wall thickness associated with an anomaly can be analyzed and normalized. Based on normalized wall thickness, a software classifier can make a more accurate classification.

In some embodiments, template matching can be performed to determine whether the anomaly matches one or more templates. Again, the template matching characteristics can be used by a software classifier for more accurate classification of a candidate anomaly. Template matching can also be used to eliminate certain areas from consideration.

Any of the above characteristics can be used as input to a classifier, such as a rule-based system, a neural network, or a support vector machine. The classifier can draw upon the various characteristics to provide a classification of the candidate anomalies (e.g., as being of interest or not being of interest).

The technologies can be applied to any of a variety of anatomical structures, such as the colon, bronchus, blood vessels, bladder, urinary tract, billiary tract, cerebrospinal spinal fluid containing spaces of the brain, paranasal sinuses, chambers of the heart, or the like.

Additional features and advantages of the invention will be made apparent from the following detailed description of illustrated embodiments, which proceeds with reference to the accompanying drawings.

BRIEF DESCRIPTION OF THE DRAWINGS

FIGS. 7A-7D are views of exemplary candidate anomalies having exemplary curvatures.

FIG. 8 is a flowchart showing an exemplary method for measuring wall thickness.

FIG. 9 is a graph showing an exemplary intensity profile.

FIGS. 12A-12D are graphs of exemplary intensity profiles used to calculate wall thickness.

FIGS. 13A-13C are further graphs of exemplary intensity profiles used to calculate wall thickness.

FIGS. 15, 16, and 17 are views of exemplary templates for template matching techniques.

DETAILED DESCRIPTION

Definitions

An anomaly of interest includes any abnormal feature occurring in an anatomical structure. Anomalies can include surface anomalies (e.g., wall surface anomalies). For example, anomalies of interest include any number of cancerous or pre-cancerous growths, lesions, polyps, or other features. In a fully automated system, the location or image of an anomaly of interest can be provided as a result. In a system with user (e.g., physician) assistance, the anomaly of interest can be presented to the user for confirmation or rejection of the anomaly as being of interest. Those anomalies confirmed as of interest can then be provided as a result.

Classifying includes designating an anomaly as of interest or designating an anomaly as not of interest (e.g., disqualifying a candidate anomaly as being of interest). For example, in the case of a virtual colon, an anomaly can be classified as a polyp. In the example of a virtual bronchus, an anomaly can be classified as a lesion.

A representation of an anatomical structure includes any digital representation of an anatomical structure (or portion thereof) stored for processing in a digital computer. For example, representations can include two- or three-dimensional representations of an anatomical structure stored as an image via a variety of data structures. Representations can be composed of pixels, voxels, or other elements. Such a representation is sometimes called "virtual" (e.g., a "virtual colon") because it is a digital representation that can be analyzed to learn about the represented anatomical structure.

Overview of Technologies for Detecting Anomalies of Interest

Figure 1:
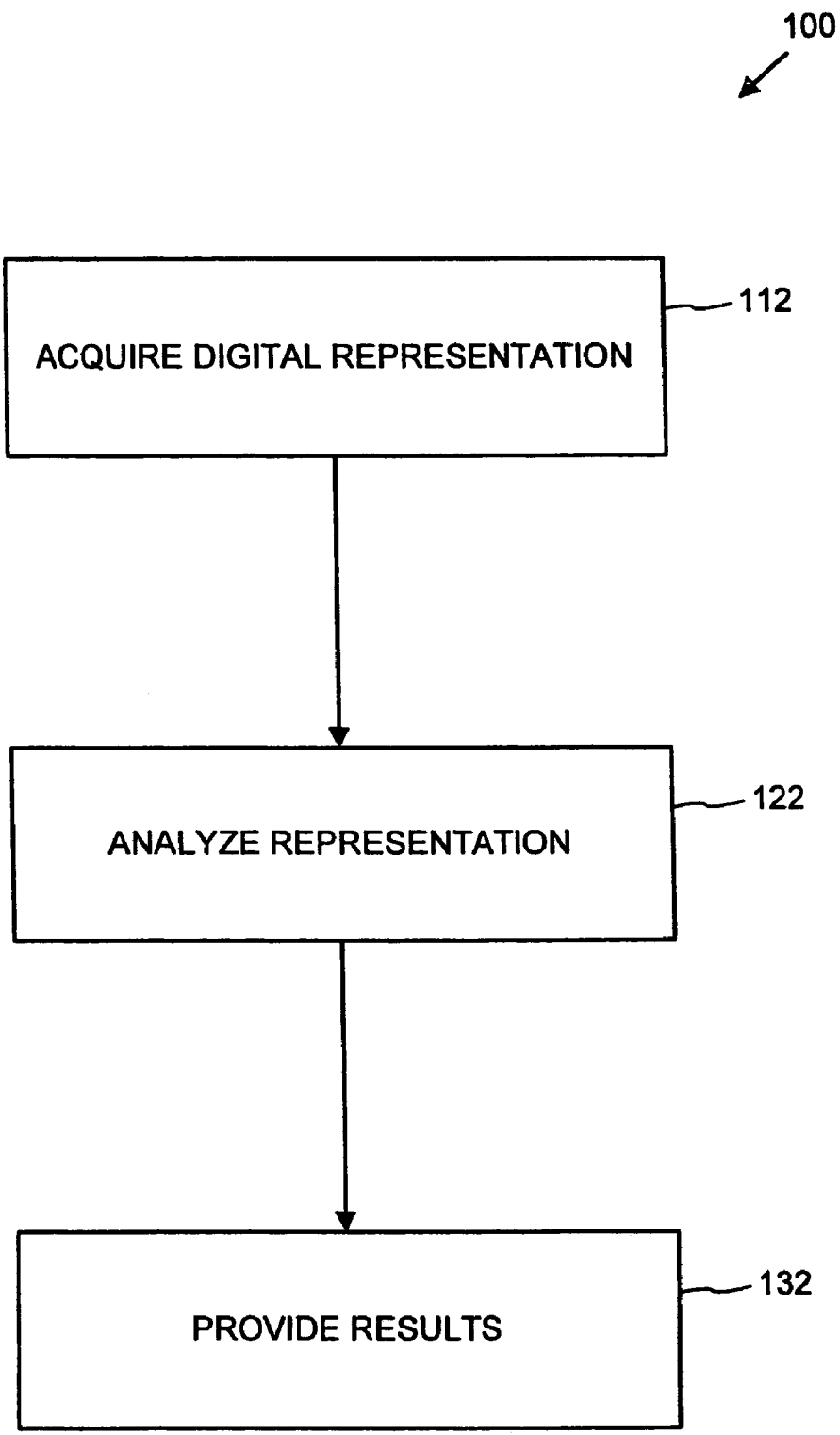
FIG. 1 is a flowchart showing an exemplary method for detecting anomalies of interest in an anatomical structure.

An overview of an exemplary method 100 for detecting anomalies of interest in an anatomical structure is shown in FIG. 1. The actions shown in the method 100 can be performed in computer software.

At 112, a representation of the anatomical structure is acquired. For example, a CT scan can be taken of a human patient to acquire image slices of the patient's colon. Various preprocessing can be performed on the representation as desired. For example, the slices can be combined to form a three-dimensional image.

At 122, the representation is analyzed to detect anomalies of interest. For example, in the case of a virtual colon, polyps can be detected.

At 132, the results are provided. For example, sites where anomalies of interest appear can be presented for consideration by a physician.

Overview of Representations of Anatomical Structures

Acquisition of a representation of an anatomical structure is typically done by performing a scan of the soft tissues of the patient. For example, a CT scan can be performed according to any number of standard protocols. CT scans can be used to generate thin-section CR data (e.g., helical scan CT data). The representation can be analyzed immediately after the scan, or the representation can be stored for later retrieval and analysis. Exemplary techniques for acquiring scans are described in Vining et al., "Virtual Colonoscopy," *Radiology* 193(P):446 (1994), Vining et al., "Virtual Bronchoscopy," *Radiology* 193(P):261 (1994), and Vining et al., "Virtual bronchoscopy. Relationships of virtual reality endobronchial simulations to actual bronchoscopic findings" *Chest* 109(2):549-553 (February 1996), all of which are hereby incorporated herein by reference.

Any number of hardware implementations can be used to acquire a representation of an anatomical structure. For example, the GE Advantage (e.g., high speed) scanner of GE Medical Systems, Milwaukee, Wis. can be used.

Figure 2:
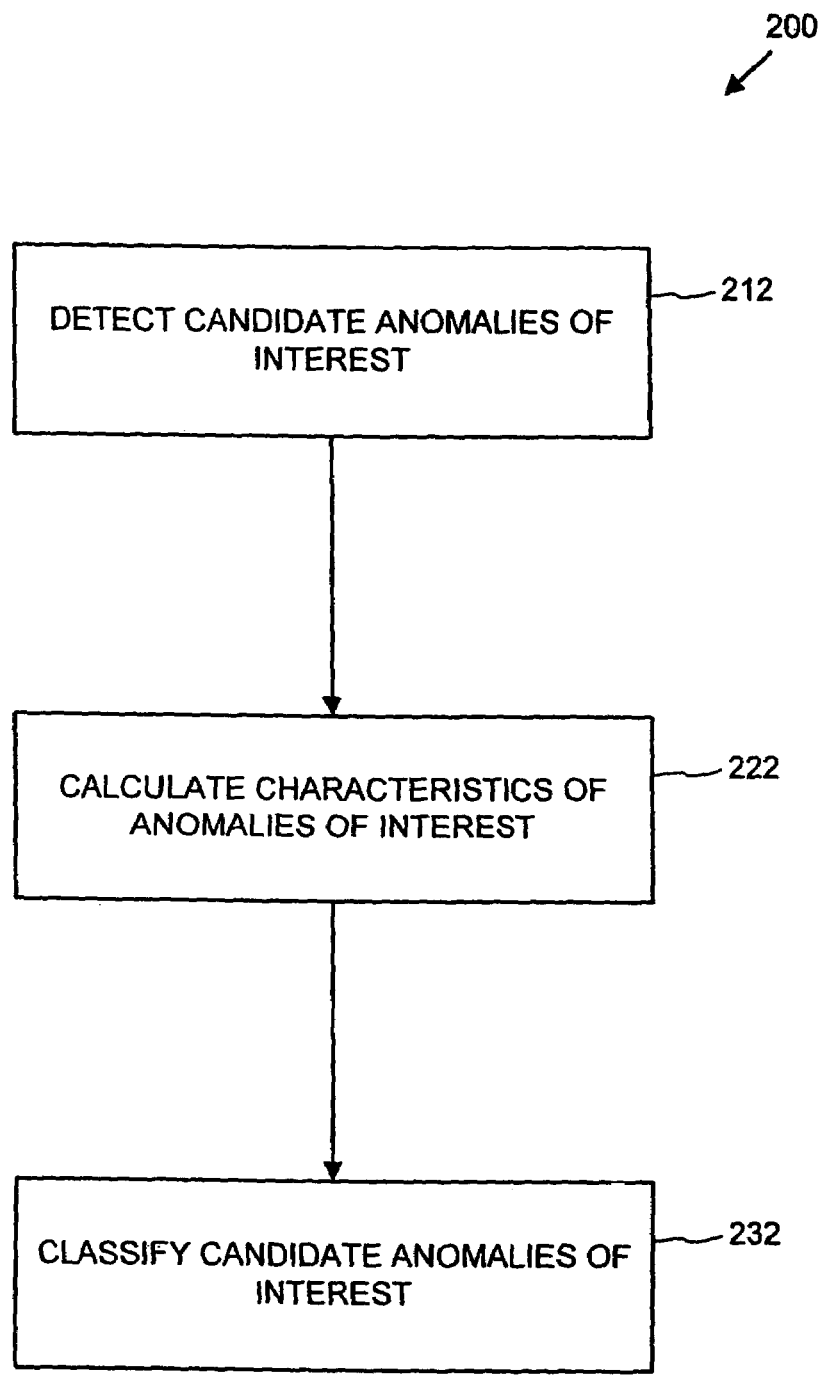
FIG. 2 is a flowchart showing an exemplary method for analyzing a representation of an anatomical structure to detect anomalies of interest in the anatomical structure.

Overview of Analyzing a Representation of an Anatomical Structure to Detect Candidate Anomalies of Interest An overview of an exemplary method 200 for analyzing a representation of an anatomical structure to detect anomalies of interest in the anatomical structure is shown in FIG. 2. The actions shown in the method 200 can be performed in computer software.

At 212, candidate anomalies of interest are detected in the representation of the anatomical structure. For example, curvatures related to the structure can be computed and portions of the structure exhibiting a particular curvature type can be designated as a candidate anomaly of interest.

At 222, one or more characteristics of the detected candidate anomalies of interest are calculated. For example, size, shape, or any number of other characteristics may be relevant.

At 232, based on the characteristics of the candidate anomalies, the candidate anomalies are classified. For example, the candidate can be classified as "of interest" or not "of interest." Sometimes such classification is described as "eliminating false positives." Classification can be done in many ways. For example, a candidate anomaly of interest may be designated as "of interest" only if it meets certain criteria or is so classified by a software classifier. Or, the candidate anomalies can be ranked according to a scoring system.

Exemplary Characteristics of Candidate Anomalies of Interest

Exemplary characteristics of candidate anomalies of interest include those related to the anomaly's neck, normalized wall thickness associated with the anomaly, and template matching. Given a representation of an anatomical structure or a region of such representation associated with a candidate anomaly of interest, software can calculate any number of these or other characteristics for use in classification of the candidate anomaly of interest.

Overview of Anomaly Neck Characteristics

Figure 3:
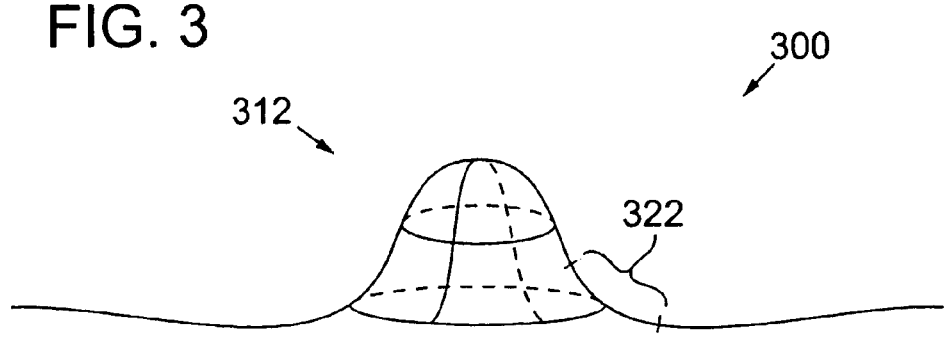
FIG. 3 depicts an exemplary candidate anomaly of interest and the neck associated therewith.

FIG. 3 shows a portion 300 of a representation of an anatomical structure that includes an exemplary anomaly 312 and a neck 322 associated therewith. Candidate anomalies of interest can be processed by software to first identify the neck 322 and then measure various characteristics of the neck.

The neck 322 can be identified in any of a number of ways, such as finding areas of hyperbolic curvature associated with the candidate anomaly of interest 312 or using deformable models. Characteristics to be measured can include size (e.g., height, circumference, area enclosed by the neck), angle, orientation, irregularity, curvature, or relation of neck to adjacent haustral folds, if applicable.

Identification of the neck 322 (or failure to identify the neck 322) and any of the neck characteristics can then be used to advantage during classification of the candidate anomaly of interest 312.

Overview of Automated Wall Thickness Measurement

A variety of automated techniques can be used to measure wall thickness associated with an anomaly. One such technique is described in Vining et al., U.S. Pat. No. 5,920,319, filed Jul. 6, 1999, entitled "Automatic analysis in virtual endoscopy," which is hereby incorporated by reference herein. However, a number of issues arise when calculating wall thickness.

Figure 4:
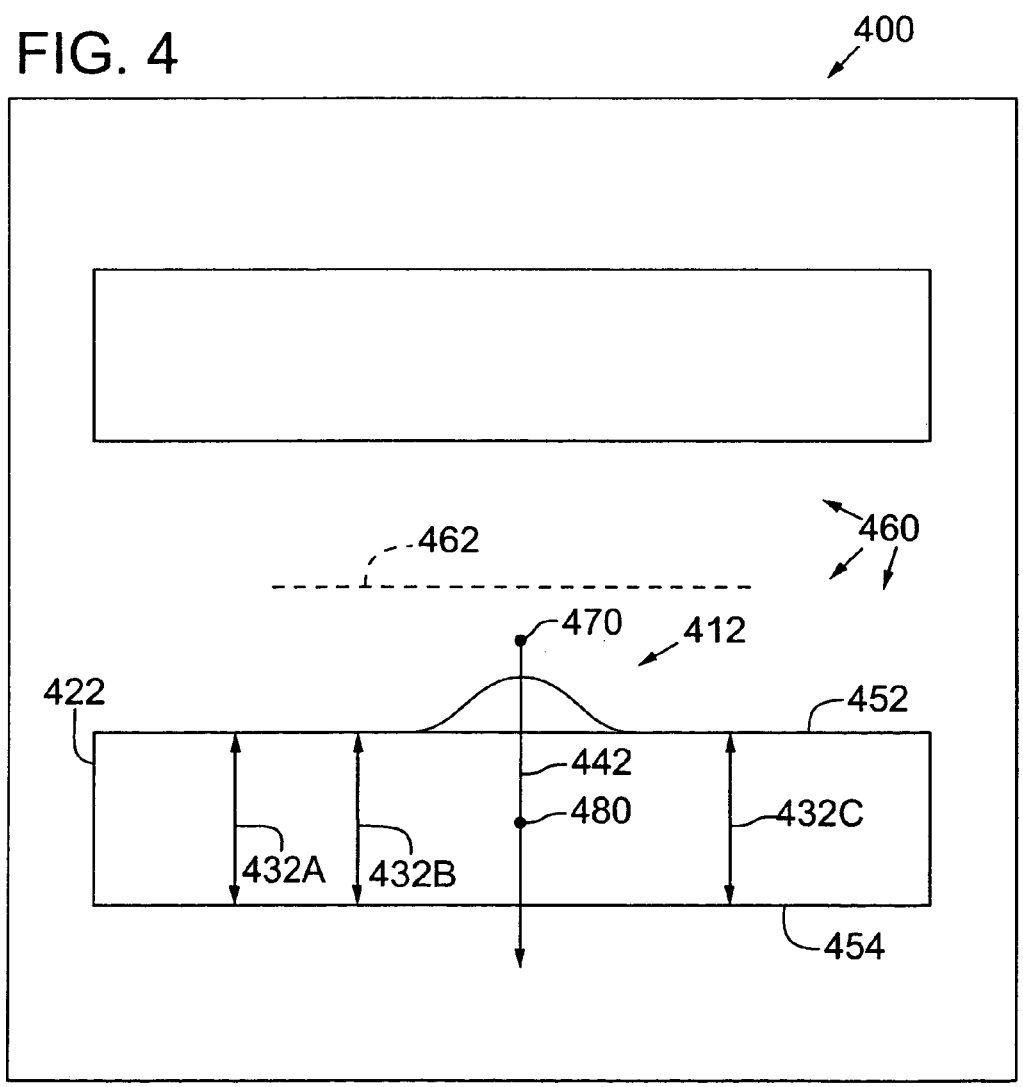
FIG. 4 depicts an exemplary candidate anomaly of interest and wall thickness associated therewith.

FIG. 4 shows a portion 400 of a representation of an anatomical structure including a candidate anomaly of interest 412 which is located on a wall 422 of the anatomical structure. It may be desirable to measure wall thickness at a variety of locations (e.g., 422, 432A, 432B, and 432C), including the wall thickness at the anomaly 412 itself.

One way to measure wall thickness is to extend a normal 442 to an approximating surface of the inner edge 452 of the wall. Voxel intensity along the normal can be measured to identify the location of the inner edge 452 of the wall and the outer edge 454 of the wall, from which wall thickness can be calculated.

At the outset, it should be noted that constructing the normal 442 can be challenging. Various techniques (e.g., gradients and patch fitting) can be used to assist in constructing the normal 442.

Further, identifying the location of the inner edge 452 of the wall or the outer edge 454 of the wall within the digital representation 400 can be problematic due to blending with adjacent structures and other tissues. Due to the environment in which the anatomical structure resides (e.g., the human body), the wall boundaries are often not clear. A number of rules can be constructed to assist in accurately finding the locations so wall thickness can be properly calculated, and initial assessments may need to be corrected.

Overview of Automated Wall Thickness Normalization

One technique of assessing wall thickness is to normalize the thickness. For example, a plurality of wall thickness measurements (e.g., using the techniques described herein) at a plurality of sites regional (e.g., proximate) to a particular wall site can be made. The normalized wall thickness can then be calculated according to a formula, such as (1):

$$\frac{W_P - W_R}{\sigma_R} \quad (1)$$

where $W_P$ is wall thickness at a particular site, $W_R$ is regional wall thickness, and $\sigma_R$ is the standard deviation of the regional wall thickness values.

Various techniques for finding regional wall thickness can be used. For example, an annulus around a candidate anomaly of interest can be used.

The normalized wall thickness measurements associated with a candidate anomaly of interest can then be fed to a classifier by which the candidate anomaly of interest is classified. An atlas of normal wall thicknesses can be used to further advantage (e.g., based on gender, age, or body habitus).

The technique of wall thickness normalization can also be useful when depicting the representation of the anatomical structure for consideration by a human observer (e.g., to a physician). For example, regions proximate to an identified anomaly or the anomaly itself can be depicted in color(s) based on the normalized wall thickness of the region to assist in drawing the physician's eye to regions having a potential anomaly of interest.

Overview of Automated Template Matching

Another measurement useful for classification can be performed via template matching. Generally, a template can be developed that shares shape characteristics with known anomalies of interest. A candidate anomaly of interest can then be compared to the template to obtain a measurement.

Templates can be two- or three-dimensional and typically are capable of being matched against a candidate anomaly of interest to determine how the anomaly is to be classified. The digital template can be shifted, rotated, or sized as appropriate depending on circumstances. Nonrigid template matching can be acquired including other transformations (e.g., affine and non-affine) so that other shapes of interest can be detected.

As a byproduct of template matching, other useful measurements can be collected, such as finding the center of a candidate anomaly of interest, the radius of the anomaly, the orientation of the anomaly, and the cross-sectional area or volume of the anomaly.

Another useful scenario to which template matching can be applied is to eliminate from consideration regions of the digital representation known not to be of interest. For example, in a colonography scenario, a template of the rectal tube can be used to eliminate the rectal tube from consideration.

Overview of Automated Classification of Candidate Anomalies of Interest

Any of the characteristics described herein can be measured and used for classifying candidate anomalies of interest via a software classifier. A variety of thresholds can be set based on observed performance of the classifier.

The software classifier can take the form of a rule-based system, a neural network, or a support vector machine. The classifier can draw upon the various characteristics described herein to classify the candidate anomalies. Specialized classifiers can be implemented to classify anomalies within a particular anatomical structure (e.g., colon, bronchus, and the like).

Overview of Presenting Results

Candidate anomalies of interest confirmed as being of interest can be provided in a number of ways. For example, they can be presented in a digital gallery of images. Color coding can be used to indicate which region of an anomaly was determined to be the anomaly neck.

Details of Exemplary Implementation

Detecting Candidate Anomalies of Interest

Any number of techniques can be used to analyze a representation of an anatomical structure to detect candidate anomalies of interest. One such technique uses curvature and is described in U.S. Pat. No. 6,246,784 to Summers et al., filed Aug. 18, 1998, and entitled "Method for Segmenting Medical Images and Detecting Surface Anomalies in Anatomical Structures," which is hereby incorporated herein by reference. Any other approach capable of detecting anomalies in a representation of an anatomical structure can be used as an alternative.

The set of anomalies detected by such an approach can be considered candidate anomalies of interest for any of the technologies described herein. Characteristics of the candidates can then be measured as described below and used to classify the candidates (e.g., as "of interest" or "not of interest").

Details of Exemplary Implementation: Anomaly Neck

Figure 5:
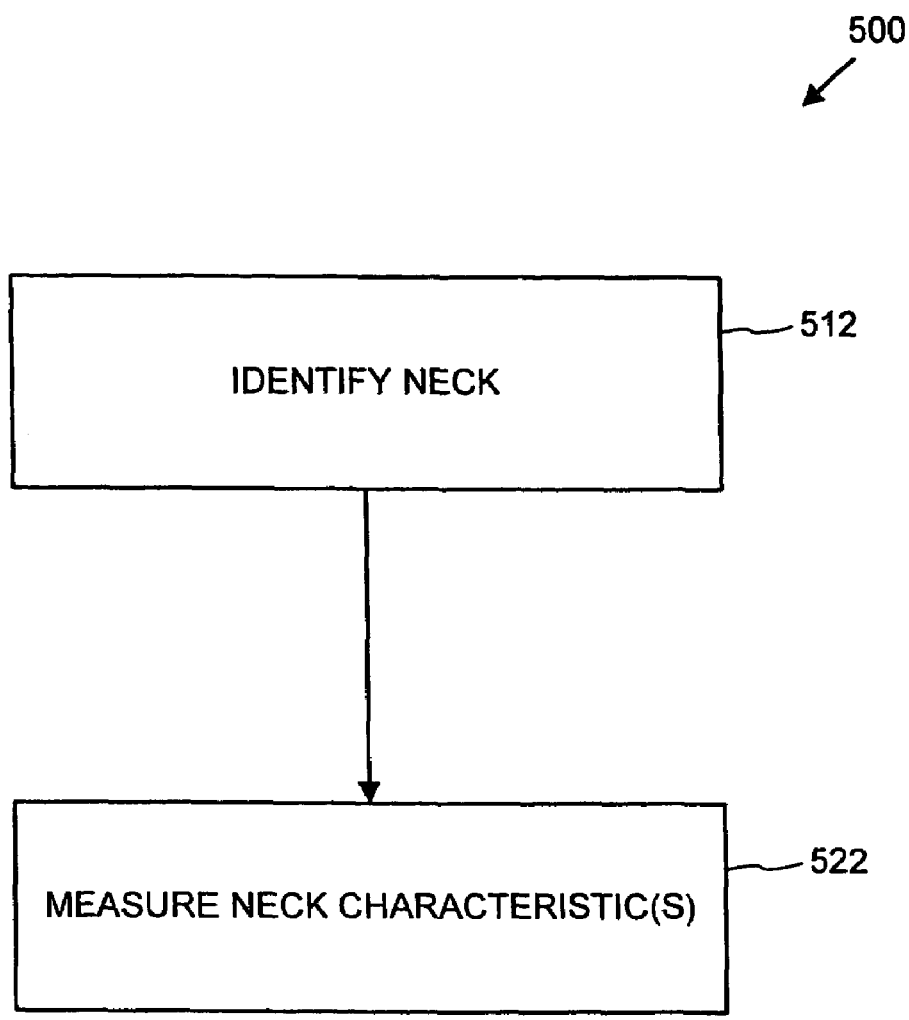
FIG. 5 is a flowchart showing an exemplary method for measuring characteristics associated with an anomaly neck.

An overview of an exemplary method 500 for measuring characteristics associated with an anomaly neck is shown in FIG. 5. The method can be performed in software. At 512, the anomaly neck is identified. For example, the area proximate an anomaly can be searched to find locations designated as part of the neck. At 522, one or more characteristics of the identified neck are measured.

Figure 6:
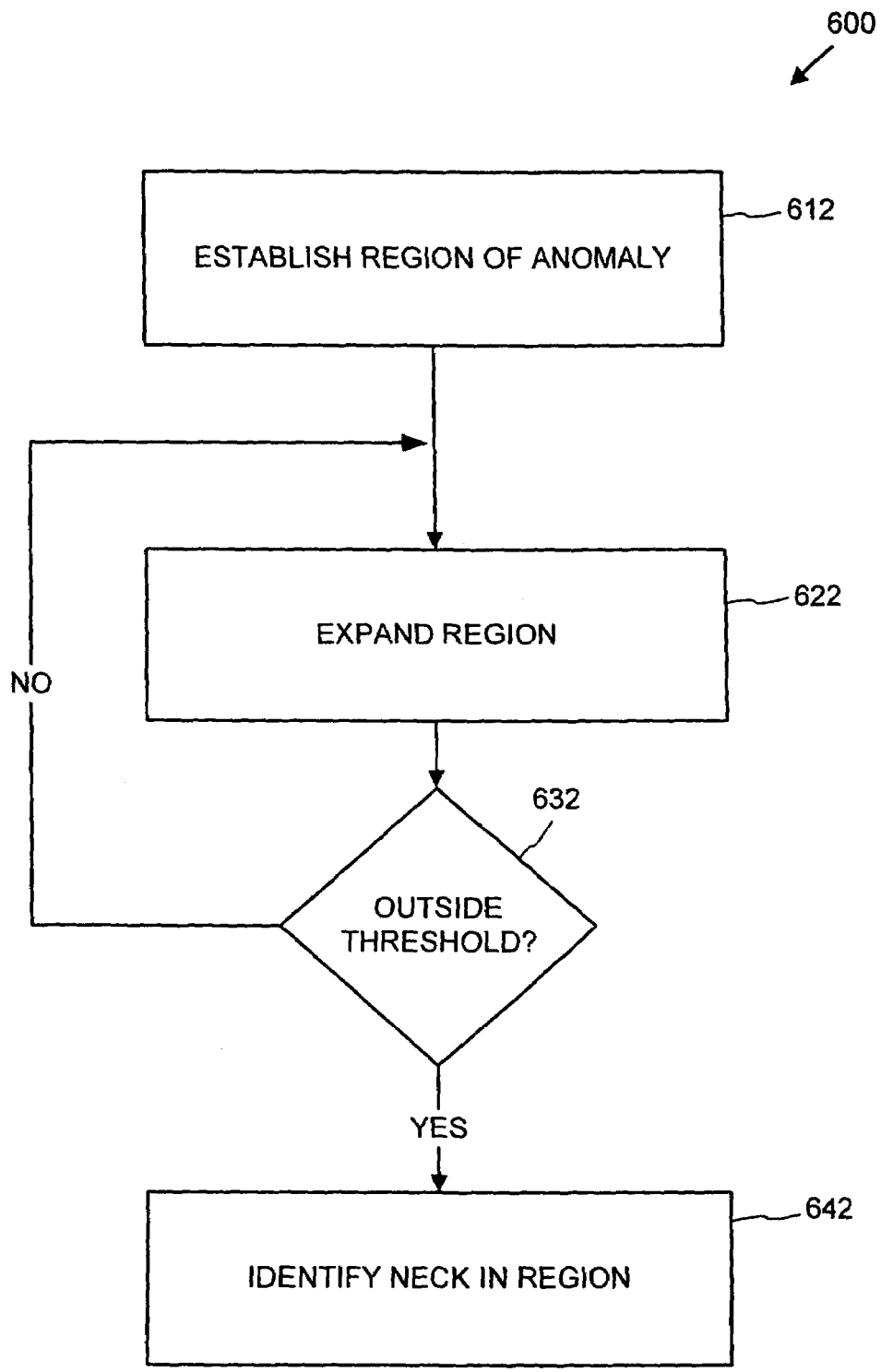
FIG. 6 is a flowchart showing an exemplary method for identifying an anomaly neck.

An exemplary method 600 for identifying a neck, such as described in 512 above is shown in FIG. 6. The method can be performed by software.

At 612, the location of an anomaly is established. For example, the boundary of a region designated by an anomaly detector can be established. In the example of an anomaly detected by identifying elliptical curvature of the peak type, the boundary of the region exhibiting elliptical curvature of the peak type can be used. For example, a closed loop around the region can be drawn by software. Or, a region (e.g., center point) within such curvature can be used.

At 622, the region is expanded. For example, a series of subsequent loops (e.g., while preserving continuity by the loop) can be formed further away from the original region (e.g., the region having elliptical curvature of the peak type).

At 632, a test is made to see if the region has been sufficiently expanded. For example, a pre-determined maximum distance can be used. Instead of using Euclidean distance, the distance can be measured along the surface (e.g., the smallest distance between a point of a loop defining the region and any point on the boundary of the original region). If the region has not been sufficiently expanded, expansion continues at 622.

After the region has been sufficiently expanded, the neck is identified within the region at 642. The identification need not be a separate action as shown; it can be done in concert with the earlier actions (e.g., while expanding the region). Instead of using the loop process described, deformable models can be used.

To identify the neck, curvature criteria can be used. For example, those points on the loops described above having hyperbolic curvature (e.g., a saddle point) within a pre-designated range can be included in the anomaly neck.

Having identified the neck, one or more characteristics of the neck can be measured. Exemplary neck characteristics include the following: neck size, neck height, circumference of neck, area enclosed by neck, angle of neck, orientation of neck, irregularity of neck, curvature of neck, and relation of neck to adjacent haustral folds (e.g., whether abutting a fold or on a fold).

As a by-product of measuring certain characteristics of the anomaly neck, various other characteristics related to the anomaly can be measured. For example, when determining the orientation of the neck, a plane can be fit to the circumference of the neck. Fitting a plane to the circumference of the neck can then be used to determine the base of the anomaly for purposes of measuring the depth of protrusion of the anomaly or the anomaly height.

Irregularity of the neck can be measured. For example, a fractal technique or some other measure of jaggedness can be used.

Curvature assessment can take a variety of forms. For example, Gaussian curvature, mean curvature, principal curvature, shape index, and curvedness can be derived by processing curvature values. In a scenario involving a three-dimensional representation, such measurements can be calculated using partial derivatives, finite differences, convolution kernels, or by fitting of approximating curves or surfaces. For example, if a neck angle for an anomaly is acute, the maximum principal curvature may be large, and such a measurement can be used to distinguish a true positive from a false positive.

The above techniques can also be used in scenarios involving a two-dimensional representation of an anatomical structure. In such scenarios, the anomaly, adjacent wall, or interface with a lumen of the anatomical structure can be segmented (e.g., via an edge detection filter). Then, the angle made by the junction of the fleshy portion of the anomaly and the inner edge of the wall of the anatomical structure can be measured. Alternatively, or in addition, isosurface and level set techniques can be used to identify the desired edge of the anomaly and the inner anatomical structure wall.

Measurement can also or alternatively be performed at locations other than the junction described above. For example, measurement can be made within the junction, adjacent to the junction, within the anomaly, or on the anatomical structure wall, along an outer edge of the wall, or in close proximity to the wall or the anomaly.

The minimum principal curvature can also be used to assess anomaly size. Also, by fitting the anomaly base to a shape (e.g., an ellipse), the eccentricity or aspect ratio can be measured, which can be useful for distinguishing anomalies of interest from folds in the anatomical structure.

Any of the above neck or other measurements can be used to classify or assist in classifying a candidate anomaly (e.g., with any of the classifiers described herein). For example, in the case of a virtual colon, the neck or other measurements can be used to classify or assist in classifying an anomaly as a polyp.

Exemplary Implementation: Maximum Principal Curvature of Polyp Neck

A set of over 24,000 anomalies known to be false positives and 38 anomalies known to be true positives in colon-related data were analyzed by measuring the maximum principal of the anomaly (e.g., polyp) neck. The area under the ROC curve for the average value of the maximum principal curvature of the neck was 0.67.

Details of Exemplary Implementation: Exemplary Curvatures

Views of exemplary candidate anomalies of interest are shown in FIGS. 7A-7D. A side view of a candidate anomaly of interest 710 is shown in FIG. 7A. Some regions (e.g., surfaces) 712 and 714 of the anomaly 710 have elliptical curvature of the peak type, and such elliptical curvature can be used by the software to identify the candidate anomaly when processing a digital representation of an anatomical structure. Other regions (e.g., surfaces) 716 and 718 have hyperbolic curvature and are thus identified as being part of the anomaly neck.

A top view of the candidate anomaly of interest 710 is shown in FIG. 7B. Again, the same regions (e.g., surfaces) 712 and 714 of the anomaly 710 have elliptical curvature of the peak type, and such elliptical curvature can be used by the software to identify the candidate anomaly. Other same regions (e.g., surfaces) 716A, 716B, 718A, and 718B have hyperbolic curvature and are thus identified as being part of the anomaly neck. In the example, the candidate 710 was classified as an anomaly of interest (e.g., a polyp or "true positive").

A side view of a candidate anomaly of interest 730 is shown in FIG. 7C. Some regions (e.g., surfaces) 732 and 734 of the anomaly 710 have elliptical curvature of the peak type, and the software can identify such regions to identify the candidate anomaly. Other regions (e.g., surfaces) 736 and 738 have hyperbolic curvature and are thus identified as being part of the anomaly neck.

A top view of the candidate anomaly of interest 730 is shown in FIG. 7D. The same regions (e.g., surfaces) 732 and 734 of the anomaly 730 have elliptical curvature of the peak type, and the software can identify such regions to identify the region as a candidate anomaly. The other same regions (e.g., surfaces) 736 and 738 of the anomaly 730 have hyperbolic curvature and are thus identified as being part of a neck of the anomaly 730. In the example, the candidate 730 was classified as an anomaly not of interest (e.g., a "false positive").

The candidate 710 is classified as an anomaly of interest because the curvature of the neck (e.g., regions 716, 716A, 726B, 718, 718A, and 718B) is greater than that of 730 (e.g., regions 736 and 738). For example, the region 736 is less highly curved than the region 718. Although the example in FIG. 7A shows that the head of the candidate 710 is larger than the diameter of the neck, such is not necessary for classification as an anomaly of interest. For example, a key attribute for classification can be curvature of the neck.

Details of Exemplary Implementation: Measuring Wall Thickness

The ability to accurately measure wall thickness can be beneficial for various of the techniques described herein. Such measurements are often challenging because other structures or features in the digital representation of an anatomical structure make it difficult to determine the orientation of the wall and the location of the inner and outer portions (e.g., boundaries) of the wall.

One possible way to measure wall thickness is to draw a normal to the wall and then evaluate the intensity of voxels or pixels along the wall. An exemplary method 800 for measuring wall thickness is shown in FIG. 8. The method 800 can be performed by software.

At 812, a normal to the wall being measured is calculated. For example, given a point, a ray is drawn through the wall perpendicular to the wall (e.g., perpendicular to the wall surface).

At 822, an intensity profile is generated. For example, voxel intensities along the normal can be measured.

At 842, the intensity profile is evaluated to determine wall thickness. Because the initial point from which the normal is drawn may be in a void (e.g., air 460 of FIG. 4) or within the anatomical structure walls (e.g., between the inner edge 452 of the wall and the outer edge 454 of the wall of FIG. 4), analysis of the intensity profile can be done to allow for such scenarios as well as other scenarios.

An exemplary intensity profile 900 is shown in FIG. 9. The x-axis represents distance away from the starting point (e.g., point 470 of FIG. 4) along the normal, and the y-axis represents the voxel intensity at a point on the normal at such a distance. Typically, a higher intensity indicates higher density within the anatomical structure. So, for example, a very low intensity typically indicates a void or air. Using various thresholds and rules, a point 921 on the profile representing the inner edge of the wall can be calculated, and a point 922 on the profile representing the outer edge of the wall can be calculated. The wall thickness can then be calculated by computing the distance 932 between the two points. The region 940 represents a region of the digital representation beyond (e.g., outside) the wall. For example, the region 940 might indicate another portion of the anatomical structure if the structure winds (e.g., folds) onto itself.

With reference to FIG. 4, gradients can be computed to determine the normal 442. For example, average gradients over small regions can be computed. Alternatively, a computed center line 462 can be computed from which the normal 442 can be generated by measuring perpendicular lines.

Other techniques, such as fitting surface patches (e.g., b-spline or other approximating patches) to the inner edge 452 of the wall or the outer edge 454 of the wall, the anomaly 412 or within close proximity thereto can be used. Differentiation, cross products of vectors lying within a plane tangent to the point of interest, or other mathematical methods can then be used to compute the normal 442.

Having calculated the normal 442, the location of the inner edge 452 of the wall (e.g. an inner surface) can be identified. The precise location of the inner edge of the wall is sometimes uncertain due to volume averaging artifact and blending of adjacent structures within a voxel. Such adjacent structures may be large relative to the thickness of the wall. Various rules can be used to evaluate the intensity profile.

For example, in situations where the voxel intensity along the ray (e.g., from the point 442) reaches that of water or soft tissue density (e.g., 0 HU to 60 HU), the inner edge of the wall of the anatomical structure can be set at a point midway between that of air (−1,000 to −1,024 HU) and soft tissue (0 to 60 HU). However, when voxel intensities along the ray do not reach soft tissue intensity and when volume averaging artifact is suspected, the location of the inner edge of the wall can be set midway between that of air and the peak voxel intensity along the ray. In both of these situations, an upper limit on the ray distance is used to avoid straying far from the expected location of the outer edge of the wall of the colon. For example, upper limits of one or two centimeters may be useful.

Then, the outer edge of the wall can be located, which may involve additional heuristics. When the outer edge of the wall of the anatomical structure (e.g., a colon) abuts fat, the location of the outer edge of the wall may be set to the midpoint between soft tissue attenuation and fat (−100 HU). However, due to volume averaging artifact, the wall may be so thin as to never reach soft tissue attenuation. In such a scenario, voxel intensities along the ray may not exceed fat attenuation. If so, the outer edge of the wall can be set to the first fat voxel. In cases of volume averaging artifact where even fat attenuation levels are not reached, the location of the outer edge of the wall may be set to the location of the peak voxel intensity. Locations and voxel intensities can be computed using floating point numbers and trilinear or other interpolation methods in order to improve accuracy.

Details of Exemplary Implementation: Rules for Measuring Wall Thickness

Figure 10:
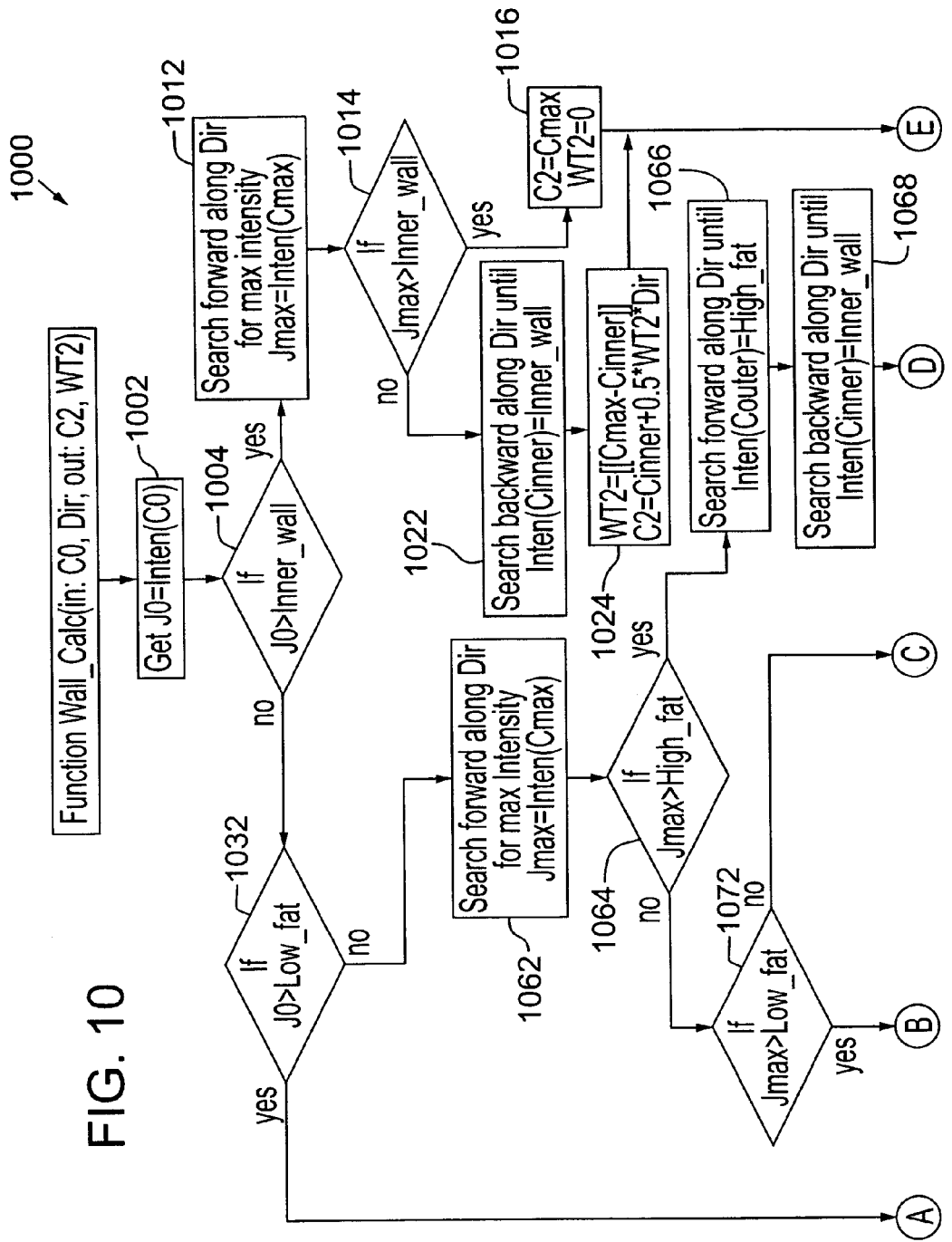
FIGS. 10 and 11 are a flowchart showing an exemplary method for calculating wall thickness.
Figure 11:
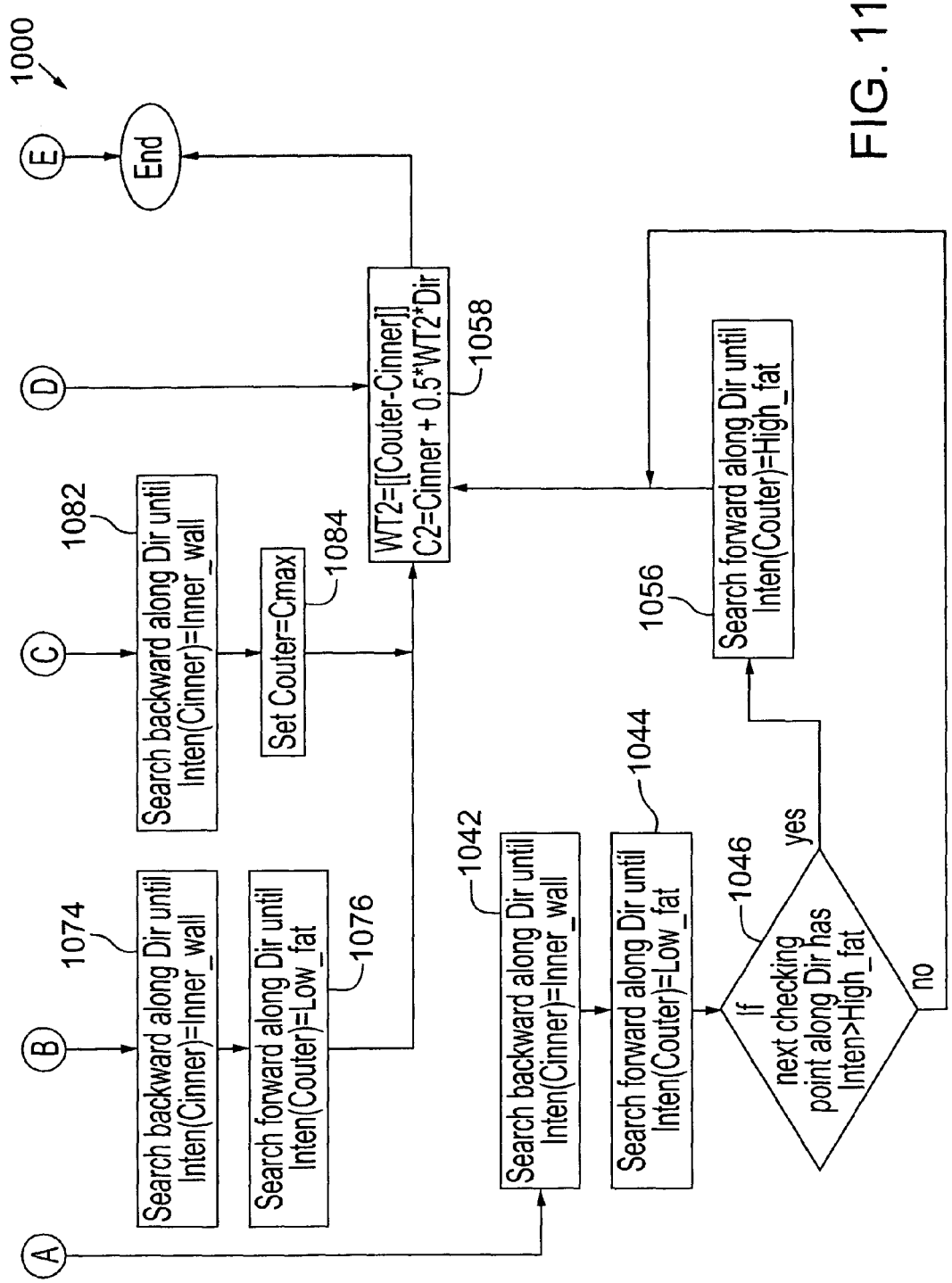

An exemplary detailed method 1000 for calculating wall thickness from an intensity profile is shown in FIGS. 10 and 11 in the function Wall_Calc(in:C0, Dir; out: C2, WT2). The method 1000 can be implemented in software via any number of programming languages.

On a general level, the method can analyze voxel intensities along a normal to the wall with reference to thresholds (e.g., the "Inner_wall" "Low_fat," and "High_fat" thresholds) to determine wall thickness. "Low_fat" indicates a lowest voxel intensity consistent with fat. "High_fat" indicates a highest voxel intensity consistent with fat, taking into account volume averaging with soft tissue (e.g., assuming soft tissue is 20 HU). Undulations of intensities can be handled in cases, for example, where the intensity profile vacillates between or within the Low_fat and High_fat regions.

The rules can take a point at an arbitrary location with respect to the surface of the wall and determine the wall thickness corresponding to the point. In some cases, the rules "backtrack" along the normal.

In the example, the function takes "C0" and "Dir" as input and produces "C2" and "WT2" as output. The function also relies on the digital representation of the anatomical structure. Intensities of voxels within the representation are acquired via the function "Inten(<voxel>)." Thresholds for "Inner_wall," "Low_fat," and "High_fat" are also relied upon. In the example, these are constants (e.g., −500, −100, and −40 HU); however, any number of other choices for these values can be similarly successful, and the technology is not limited to one set of values. If necessary, the values may be adjusted or calibrated based on the relative grayscale levels of scans.

"C0" is the point at which wall thickness is to be measured (e.g., the point 470 of FIG. 4 and is possibly the predicted or identified location of a candidate anomaly), and "Dir" is the vector (e.g., related to the ray 442) normal to the wall.

"C2" is sometimes called the corrected version of "C0" and is placed within the wall (e.g., at 480) to designate the position of the anomaly. "C0" may happen to be floating in air or embedded between the inner edge of the wall and the outer edge of the wall. WT2 is the measured wall thickness.

At 1002, voxel intensity at the point C0 is determined and stored as J0. Then, at 1004, it is determined if the intensity is less than the "Inner_wall" threshold. If so, the method continues at 1012, where a search is performed along the ray Dir for the maximum intensity; the maximum intensity is stored as "Jmax," and the corresponding point location is stored as "Cmax." At 1014, if Jmax is less than the "Inner_wall" threshold, at 1016 the corrected point C2 is set to Cmax, and the wall thickness WT2 is set to zero (0).

If, at 1014, Jmax is not less than the "Inner_wall" threshold, at 1022 a search is made backward (e.g., back to the original C0 point) until the voxel intensity is or passes that of the "Inner_wall" threshold. For example, searching can be done until the intensity equals or is less than the threshold. The location of the point is stored as "Cinner." At 1024, the wall thickness WT2 is set to the absolute value of Cmax-Cinner, and corrected point C2 is set to Cinner+ 0.5*WT2*Dir.

Returning to 1004, if J0 is not less than the threshold set for "Inner_wall," at 1032, it is determined whether J0 is greater than the threshold for "Low_fat." If so, at 1042, a backward search along the ray "Dir" is done until the intensity is equal to or passes the "Inner_wall" threshold; the location of such a voxel is stored as "Cinner." Then, at 1044, a forward search (i.e., away from the original point "C0") is performed along the ray "Dir" until the intensity is equal to or passes the "Low_fat" threshold; the location of such a voxel is stored as "Couter."

Then, at 1046, it is determined whether the next checking point (e.g., the point adjacent "Couter") has an intensity greater than the threshold for High_fat. If so, at 1056, a forward search is made until the intensity is equal to or passes High_fat. Such a point is stored as "Couter."

Otherwise, at 1058, the wall thickness "WT2" is set equal to the absolute value of "Couter"—"Cinner" and the corrected point "C2" is set to "Cinner"+0.5*"WT2"* "Dir."

Returning now to 1032, if "J0" is not greater than the threshold set for "Low_fat," at 1062, a forward search along the ray "Dir" is made for the maximum intensity voxel. The location is stored as "Cmax," and the intensity is stored as "Jmax." At 1062, if Jmax is greater than the threshold set for "High_fat," at 1066, a forward search is made along the ray "Dir" until the intensity is equal to or passes the threshold set for "High_fat." The location of such a point is stored as "Couter."

Then, at 1068, a backward search is performed along the ray defined by "Dir" until the intensity is equal to or passes the "Inner_wall" threshold. The location of such a point is stored as "Cinner." Then, 1058 is performed as described above.

Returning to 1064, if "Jmax" is not greater than the "High_fat" threshold, at 1072, it is determined whether "Jmax" is greater than "Low_fat." If so, at 1074, a backward search is done along the ray "Dir" until the intensity is equal to or passes the "Inner_wall" threshold. The location of such a point is stored as "Cinner." At 1076, a forward search is then done until the intensity is equal to or passes the "Low_fat" threshold. The location of such a point is stored as "Couter." Then, 1058 is performed as described above.

Returning to 1072, if it is determined that Jmax is not greater than the "Low_fat" threshold, at 1082, a backward search is performed until a point with intensity equal to or passing the "Inner_wall" threshold is found. The location of such a point is stored at "Cinner." Then, at 1084, the value for "Couter" is set equal to the value of "Cmax" computed in 1062. Then, 1058 is performed as described above.

Similar results can be achieved via different approaches, and variations (e.g., using thresholds other than the exemplary ones presented) can be employed.

Details of Exemplary Implementation:

Analysis of Exemplary Intensity Profiles

Exemplary Intensity Profiles are shown in FIGS. 12A-12D and FIGS. 13A-13C. In the examples, the x-axis represents a location along a normal to the wall (e.g., along a ray), and the y-axis represents voxel intensity at the location. The exemplary thresholds "High_fat," "Low_fat," and "Inner_wall" are also shown. C0 indicates the original point (e.g., for the ray generated normal to the wall). Wall thickness "WT2" is also shown (if any), and C2 indicates the location of the anomaly (e.g., because C0 was provided as the initial location of the anomaly, C2 is sometimes called the "corrected location of C0").

The corrected position can be calculated via the following formula:

$$\text{Corrected\_pos} = \text{Old\_pos} + c2 * \text{Ray} \qquad (2)$$

where Old_pos, Ray (e.g., "Dir"), and Corrected_pos are 3-dimensional vectors, and C2 is a scalar (number).

The intensity profiles can be processed according to the rules described above to generate the wall thickness and corrected anomaly locations. In the example of 12A ("Scenario I"), at the portion 1212, there are at least two subsequent points within fat (e.g., between high fat and low fat). The location 1216 is stored and thereby designated as the inner edge of the wall (e.g., "Cinner"), and the location 1218 is stored and thereby designated as the outer edge of the wall (e.g., "Couter"). In the rules described above with reference to FIGS. 10 and 11, Scenario I can be implemented via an execution path including 1032, 1042, 1046, and 1058.

In the example of 12B ("Scenario III"), the location 1226 is stored and thereby designated as the inner edge of the wall (e.g., "Cinner"), and the location 1228 is stored and thereby designated as the outer edge of the wall (e.g., "Couter"). In the rules described above with reference to FIGS. 10 and 11, Scenario III can be implemented via an execution path including 1032, 1062, 1072, and 1074.

In the example of 12C ("Scenario IIA"), the location 1236 is stored and thereby designated as the inner edge of the wall (e.g., "Cinner"), and the location 1238 is stored and thereby designated as the outer edge of the wall (e.g., "Couter"). In the rules described above with reference to FIGS. 10 and 11, Scenario IIA can be implemented via an execution path including 1032, 1062, and 1066.

In the example of 12D, ("Scenario IIB") the location 1246 is stored and thereby designated as the inner edge of the wall (e.g., "Cinner"), and the location 1248 is stored and thereby designated as the outer edge of the wall (e.g., "Couter"). In the rules described above with reference to FIGS. 10 and 11, Scenario IIB can be implemented via an execution path including 1032, 1042, and 1056.

In the example of 13A ("Scenario V"), the wall thickness is determined to be zero (0). The location of the anomaly (e.g., C2) is designated as the location 1317 of the maximum value on the curve (e.g. "Cmax") under the rules for the scenario. In the rules described above with reference to FIGS. 10 and 11, Scenario V can be implemented via an execution path including 1012 and 1016.

In the example of 13B ("Scenario IVA"), the location 1326 is stored and thereby designated as the inner edge of the of the wall (e.g., "Cinner"), and the location 1328 is stored and thereby designated as the outer edge of the wall (e.g., "Couter"). In the rules described above with reference to FIGS. 10 and 11, Scenario IVA can be implemented via an execution path including 1012, 1022, and 1024.

In the example of 13C ("Scenario IVB"), the location 1336 is stored and thereby designated as the inner edge of the wall (e.g., "Cinner"), and the location 1338 is stored and thereby designated as the outer edge of the wall (e.g., "Couter"). In the example, the location 1337 of the maximum value on the curve under the rules for the scenario ("Cmax") is used to find the location 1338 of the outer edge of the wall ("Couter"). In the rules described above with reference to FIGS. 10 and 11, Scenario IVB can be implemented via an execution path including 1032, 1062, 1064, 1072, and 1082.

As is shown in the graphs, a variety of scenarios can be dealt with effectively. Given an anomaly location, the rules can calculate the wall thickness, even if it is not known a priori whether the anomaly location is in air or within the wall. Further the described rules are able to measure wall thickness, taking into account the presence of fat layers or other structures in the digital representation of the anatomical structure.

Details of Exemplary Implementation: Normalizing Wall Thickness

Wall thickness related to a candidate anomaly is particularly of interest. The various calculations above can be done for an anomaly, based on an initial estimate of the anomaly's location as determined by detecting regions with elliptical curvature in a digital representation of an anatomical structure.

Wall thickness can be normalized as described in the formula (1), above. The calculated normalized wall thickness can be used for a variety of purposes. For example, wall thickness can be used to colorize the surface of an anatomical structure (e.g., those regions proximate candidate anomalies of interest) when presented for review by the physician. For instance, thresholds for one or two standard deviations above regional wall thickness can be used for indicating the possible presence of an abnormality.

The normalized wall thickness can also be used as an input to a classifier for distinguishing true positive from false positive candidate anomalies.

Wall thickness atlases can be represented in a database of normal wall thickness and Z-score tolerances. For example, for colon analysis, a table of values of normal wall thickness as a function of distension and location of the colon can be prepared by using normal colons. The table can be developed for different genders and age ranges. Also, it can be normalized to body habitus using body surface area or other measures of patients' size. Distensions may be computed using regional lumen volumetric measurements with or without normalization for unit length.

There are a number of ways to calculate regional wall thickness. One way is to identify the polyp neck and then to sample the wall thickness in an annulus surrounding the polyp neck. The annulus may have user-adjustable or a fixed radius. The annulus may be immediately at the polyp neck or may be set off from it by a fixed or user-adjustable radius. The radius of the annulus and the offset from the polyp neck can be set by the user, can be fixed, or can be a function of distension, colonic location, or other relevant parameter, for example, size of potential detection.

Typically, regional wall thickness measurements are most helpful when made away from sites of pathology (e.g., away from anomalies). Therefore, regional wall measurements can be restricted to points along the wall or at an approximating isosurface that have nonpolypoid shape. For example, measurements can be restricted to regions having curvature of elliptical pit, planar, cylindrical, or hyperbolic types.

Further, it is possible to detect whether regional wall thickness measurements are being made on a haustral fold. Such a determination can be fed to a classifier, and classification can be based on such a determination.

Exemplary Implementation: Normalized Wall Thickness

A set of over 24,000 anomalies known to be false positives and 38 anomalies known to be true positives in colon-related data were analyzed by measuring normalized wall thickness related to the anomaly (e.g., candidate polyp). The area under the ROC curve for normalized wall thickness was 0.64. True positive detections were twice as likely to have a normalized wall thickness greater than zero compared to false positives (58% vs. 30%). Thresholds for the Z-score (e.g., zero) can be chosen dynamically or by using neural networks.

Details of Exemplary Implementation: Template Matching

Another technique useful for classifying anomalies is template matching. In general, a detected anomaly can be matched against a digital template to find similarity. The measurement of similarity (e.g., a similarity coefficient) can be used for classification. Such templates can be built from images of actual scans (e.g., parallel CT slices with anomalies of interest) or by idealized anomalies of interest. For example, hemisphere, round plateau, and half cylinder/classic polyp templates can be created.

Figure 14:
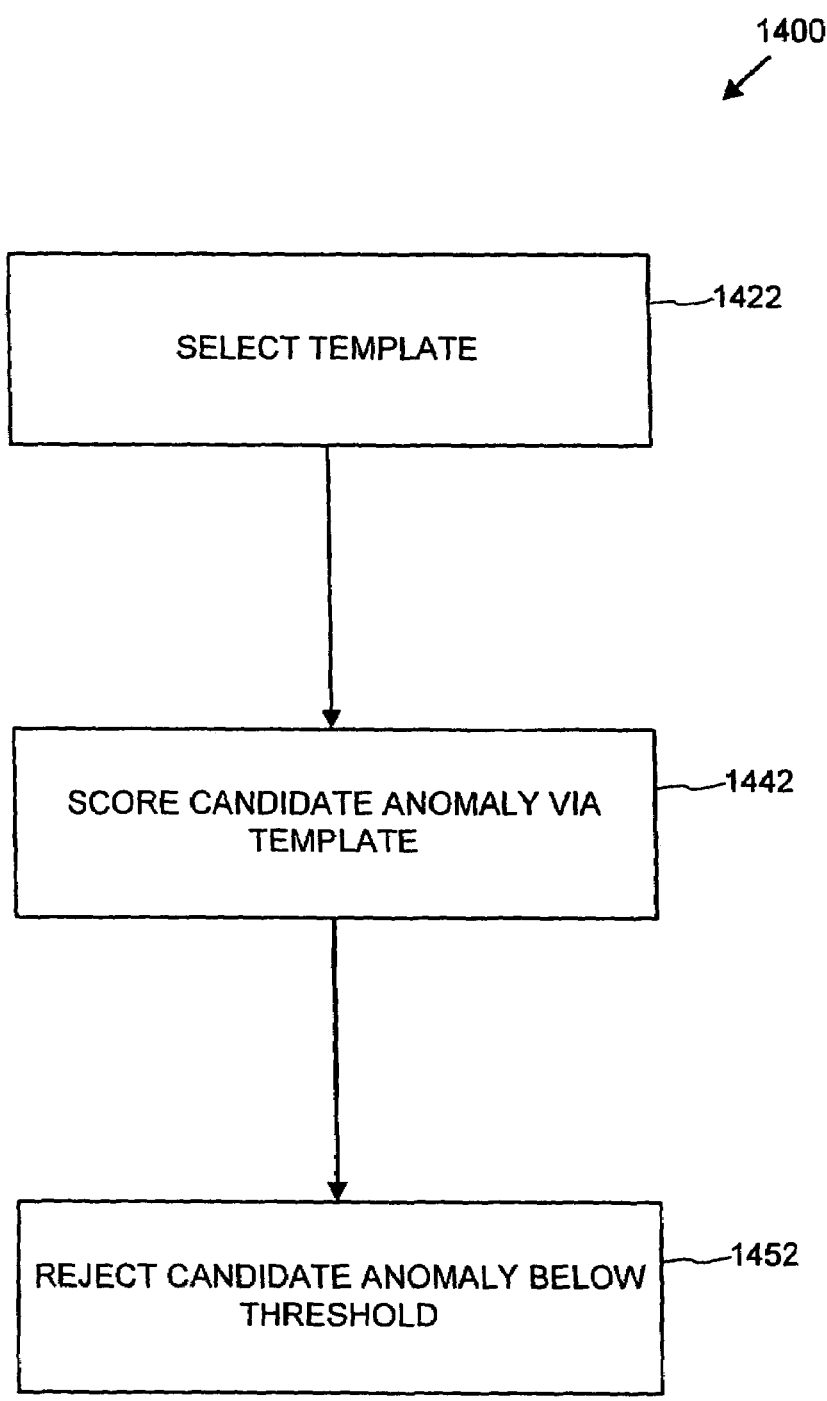
FIG. 14 is a flowchart of an exemplary method for implementing template matching to classify a candidate anomaly.

An exemplary method 1400 for template matching is shown in FIG. 14. The method 1400 can be performed by software. At 1422, a template is selected. As explained below, plural templates can be provided.

At 1442, a candidate anomaly of interest is scored via the template. For example, the template can be shifted, rotated, sized, scaled, sheared, or any combination of these in an attempt to fit it to the candidate anomaly. A similarity score is calculated.

At 1452, if the candidate anomaly has a score below a predetermined or adjustable threshold, the anomaly is rejected (e.g., denoted as not of interest). Alternatively, the score can be fed to a classifier, which considers at least the score when classifying the candidate anomaly.

Template matching can be performed in two or three dimensions. In two dimensions, the templates may be round, elliptical, square, or rectangular, varying in size from several pixels to several dozen pixels (or more), the size being fixed or variable. For example, desirable fixed dimensions are square templates that are a power of two in size. Three-dimensional templates may be isotropic or anisotropic in voxel dimension.

The templates themselves can be small images or volumes and may have any bit depth (e.g., eight, twelve, or sixteen bits). An infinite variety of templates (e.g., objects represented by the templates) are available (e.g., round, oval, spherical, or ellipsoidal shapes, sessile or pedunculated shapes, lobulated shapes or masses). Where the template is not radially symmetric, it may be desirable to orient the template according to the direction of the surface normal corresponding to the detection. Thus, a template for a sessile polyp, for example, could be oriented to match the position of the colonic wall. In addition, the template may vary as to size of the polyp, for example, radius, width of the transition from polyp to base, or angle of the polyp neck. The templates may seek to locate lucencies between the head of a polyp and its attachment to the colonic wall, for example to identify the location of the stalk for a pedunculated polyp.

While seeking to match the template against the candidate anomaly, the template may be shifted on a voxel by voxel basis to determine the maximum similarity.

Similarity may be computed using a variety of functions, including cross-correlation measures. For example, the following formula can be used:

$$Sim(a, b) = \frac{\sum_{i=0}^{n-1}(a_i - \bar{a})(b_i - \bar{b})}{\sqrt{\sum_{i=0}^{n-1}(a_i - \bar{a})^2}\sqrt{\sum_{i=0}^{n-1}(b_i - \bar{b})^2}} \quad (3)$$

where $$\bar{a} = \frac{1}{n}\sum_{i=0}^{n-1} a_i, \bar{b} = \frac{1}{n}\sum_{i=0}^{n-1} b_i \quad (4, 5)$$

"a" is for the image, and "b" is the template; "n" is the number of pixels or voxels. Further information can be found in Lee et al., "Automated Detection of Pulmonary Nodules in Helical CT Images Based on an Improved Template-Matching Technique," *IEEE Transactions on Medical Imaging*, Vol. 20, No. 7, pages 595-604 (July 2001).

The cross-correlation coefficient ranges from −1 to +1. The similarity functions need not depend on the actual intensity values, or they can depend on whether an intensity is in a particular range as denoted in the template. In this way, the shape of the intensity value distribution in the template and the candidate anomaly can be matched without regard to particular intensity values.

The similarity scores can be used for classification via a rule-based threshold or input to a more complex classifier such as a neural network or a genetic algorithm. As a result of template matching, coordinates of the center of the anomaly, its radius, its orientation, its cross-sectional area, its volume, or any combination of such values can be produced.

A shift between the template and image can be used, for example, if two series x(i) and y(i) are considered where i=0, 1, 2 . . . N−1. Then, cross-correlation r at shift d is defined as $$r(d) = \frac{\sum_i [(x(i) - mx) * (y(i - d) - my)]}{\sqrt{\sum_i (x(i) - mx)^2}\sqrt{\sum_i (y(i - d) - my)^2}} \quad (6)$$

where mx and my are the means of the corresponding series.

If the above is computed for shifts d=−(N−1), . . . , −1,0,1,2, . . . ,N−1, then it results in a cross-correlation series of twice the length of the original series. Such functions can easily be extended to two or three dimensions.

Details of Exemplary Implementation: Exemplary Templates

The templates can be constructed to be various shapes (e.g., 3D-grid) and sizes (e.g., 32×32 pixels). The templates can include features such as radius, slope, center, and general shape description. A similarity measure can be computed using the cross-correlation coefficient between the template and candidate anomalies (e.g., image slices of the anomalies). Plural similarity measures can be taken by varying the features within set of adjustable ranges. The plural similarity measures can be processed, for example, by storing the maximum value of similarity and at what template position such similarity was measured. The various features of the template, including radius and translation can also be stored.

Figure 17:
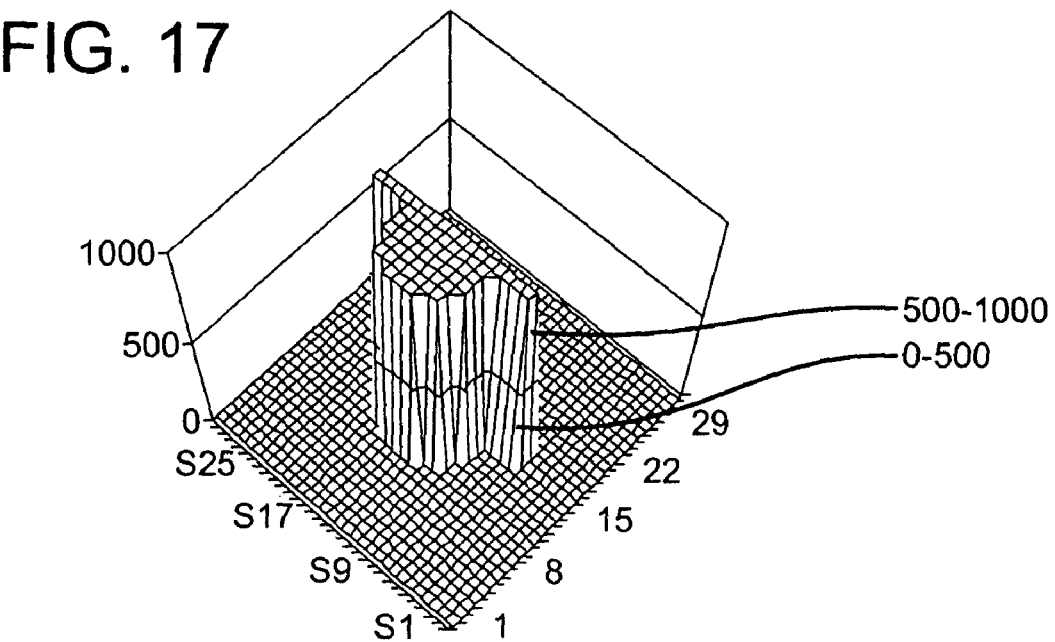

Exemplary templates are shown in FIGS. 15-17. In the example, polyp models were generated with reference to idealized anomalies of interest. The 2D images are displayed as 3D surfaces where 2 dimensions (X and Y) stand for the position of the model pixel in the polyp model image and the third dimension stands for the image function (e.g., image intensity) of the respective pixel.

FIG. 15 depicts a template being a hemisphere model. FIG. 16 depicts a template being a round plateau model. FIG. 17 depicts a template being a classic polyp model (e.g., a polyp seen in profile). Such idealized templates can be constructed via a number of software packages.

Details of Exemplary Implementation: Rectal Tube Removal

Figure 18:
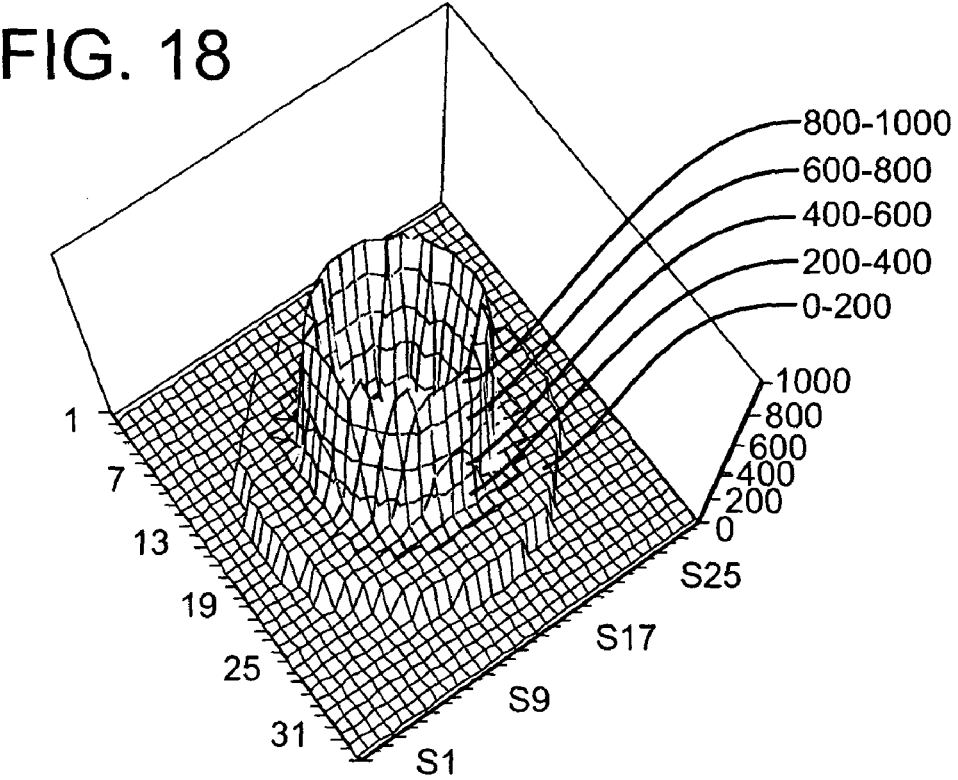
FIG. 18 is a view of an exemplary template for rectal tube removal.

Template matching can also be used for an entirely different purpose: rectal tube removal. An exemplary template shown in FIG. 18 is for matching to a rectal tube and can be used to detect the position of a rectal tube and remove it from the CT images sequence.

Similarly, a template can be constructed by which any region not to be considered can be removed from consideration. In the example, the width of the wall of the rectal tube is a parameter that can be varied.

Exemplary Implementation: Template Matching

A set of over 24,000 anomalies known to be false positives and 38 anomalies known to be true positives in colon-related data were analyzed by performing template matching via a truncated cone to detect classic round polyps. The area under the ROC curve for template similarity was 0.63.

Details of Exemplary Implementation: Other Characteristics

Based on the technologies described herein, a variety of characteristics can be measured for use by a software classifier. Exemplary characteristics are shown in Table 1. Any combination of the characteristics can be fed to a software classifier. In the example, a data structure can be constructed to represent a curved, folded surface in three-dimensional space via triangles. Nearest neighbors can be found by navigating among the triangles. A neighborhood of triangle vertices can be defined, for example, as those neighboring (e.g., connected) vertices passing a curvature test (e.g., elliptical curvature of the peak type).

TABLE 1

Characteristics

| Characteristic | Description |
| --- | --- |
| Lesion Vertices | number of vertices forming neighborhood |
| Lesion Size | distance in cm between two most separated vertices from surface neighborhood |
| Lesion Sphericity | 2*|LesionMaxAvgCurv − LesionMinAvgCurv|/ (LesionMaxAvgCurv + LesionMinAvgCurv) |
| LesionGaussianAvgCurv | (Gaussian Average Curvature) − Gauss Curv averaged over all vertices from surface neighborhood |
| LesionMeanAvgCurv | (Mean Average Curvature) − Mean Curv averaged over all vertices from surface neighborhood |
| LesionMinAvgCurv | (Min Average Curvature) − Min Curv averaged over all vertices from surface neighborhood |
| LesionMaxAvgCurv | (Max Average Curvature) − Max Curv averaged over all vertices from surface neighborhood |
| curv.min | = curv.mean − sqrt(curv.mean ** 2 − curv.gauss); |
| curv.max | = curv.mean + sqrt(curv.mean ** 2 − curv.gauss); |
| PrincCurvDiff | sqrt(LesionMeanAvgCurv ** 2 − LesionGaussianAvgCurv) |
| LesionGaussianSDCurv | std of vertices from surface neighborhood |
| LesionMeanSDCurv | std of vertices from surface neighborhood |
| LesionMinSDCurv | std of vertices from surface neighborhood |
| LesionMaxSDCurv | std of vertices from surface neighborhood |
| LesionCentroidX, Y, Z | mean over positions of vertices from surface neighborhood |
| LesionCentrodRow, Column, Slice | int indexes based on LesionCentroidX, Y, Z to nearest node in lattice |
| NewSphericity | sphericity averaged over vertices' sphericities from surface neighborhood |
| SDNewSphericity | std of NewSphericitys from surface neighborhood |
| CentroidWD | maxIntensity along ray given by mean normal (NormalX, Y, Z) − set of flexible rules chosen to determine where on ray to stop and get intensity |
| RegionDensity | averaged intensity over 12 points from diamond shaped region, centered at the same point where CentroidWD is calculated |
| SD RegionDensity | std from diamond shaped region, defined as above |
| WallThick | measured along ray (as CentroidWD), "maxIntensity − 50" rule applies to get wall thickness |

TABLE 1-continued

Characteristics

| Characteristic | Description |
| --- | --- |
| Gauss, Mean, Min, Max, NewSphericityCurvSkew | $3^{rd}$ order moment of given curvature/sphericity statistics (build for vertices forming surface neighborhood); |
| Gauss, Mean, Min, Max, NewSphericityCurvKurt | the same but $4^{th}$ order |
| Area | (in sq mm) of all full triangles constituting surface neighborhood, |
| Perimeter | total length (in cm) of island's shore line but excluding pieces like peninsula in the neighborhood |
| LenNonTriangl | total length (in cm) of pieces like peninsula, bridge on the lake |
| NumNonTriangl | total number of pieces like peninsula, bridge on the lake |
| MultiLinks | nonzero value signals topological anomaly |
| TwoLinks | number of segments which are part of any full triangle from surface neighborhood |
| OneLinks | tot number of segments which are part of at most one triangle (so, peninsula like, bridges, etc. are counted here); |
| NumTriangl | total number of full triangles constituting surface neighborhood |
| Similarity | correlation coefficient between a 2D image (32 × 32) of polyp and a model (template – like semisphere with some modifications) |
| AspectRatio | width/length of bounding box containing all vertices from surface neighborhood projected onto a plane perpendicular to NormalX, Y, Z |
| ModelRad, Xshiftt, Yshift | parameters of model for which Similarity is max (for currently used model they are radius of semisphere and shift of semisphere center with respect to the center of 32 × 32 polyp image) |
| LesionCntr2X, Y, Z | second centroid based on rules used in computing CentroidWD (midpoint between outer and inner edge of wall) |
| LesionCntr2Row, Column, Slice | int indexes based on WallThick2 to nearest node in lattice |
| WallThick2 | second wall thickness based on rules used in computing CentroidWD (distance between inner edge and outer edge of wall) |
| MeanLocWallThick2 | reported only when –N option is set and Neck neighborhood is build, it works like this: apply procedure used to calculate WallThick2 for every vertex on surface which is within certain region (like ring, centred around polyp's neck) and find mean and std (see StdLocWallThick2 below) of resulting wall thickness2 |
| StdLocWallThick2 | see MeanLocWallThick2 |
| NormedWallTh2 | (WallThick2 – MeanLocWallThick2)/ StdLocWallThick2 |
| Compactness | Area/Perimeter**2 |
| VolCurvConnect | volume (in cc) of connected voxels within a given cube around polyp which passed curvature criteria – be aware that a concept of 'connectivity' depends on the value of a flag<br>a) 0 (default for flag) takes the largest segment of hard connected voxels with accepted curvature within a cube;<br>b) 1 takes voxels with accepted curvature within a cube;<br>c) 2 takes voxels with accepted curvature which are connected via a mask within a cube |
| VolCurvMass | total mass of connected voxels (i.e. sum of intensity) |
| VolCurvDens | VolCurvMass/number of connected voxels (so, it's mass per voxel) |
| VolCurvGauss__Avg, __Std | average and std of gauss curvatures determined from connected voxels |
| VolCurvMean__Avg, __Std | as above for mean curv |
| VolCurvMax__Avg, __Std | as above but for max curv |
| VolCurvMin__Avg, __Std | as above but for min curv |
| NormalX, Y, Z | mean normal, averaged over all normals from surface neighborhood |

TABLE 1-continued

Characteristics

| Characteristic | Description |
| --- | --- |
| CmassCMass_X, _Y, _Z | [sum over i: m_i * (x, y, z)_i]/VolCurvMass where sum is over all connected voxels and m_i is intensity of a given voxel; |
| RadiusInertia | calculated with respect to axes coming through CmassCMass and LesionCentroid – radius of inertia R is defined as TotMass * R**2 = {sum over i} m_i * r_i **2 |

For CentroidWD, there are at least five possible scenarios which depend on maxIntensity and 3 constants: INNER_WALL_THRESHOLD=−500 HU, LOW_FAT_THRESHOLD=−100 HU, HIGH_FAT_THRESHOLD=−40 HU. The scenarios are as follows:

TABLE 2

Scenarios

| Scenario | Description |
| --- | --- |
| I (e.g., FIG. 12A) | LOW_FAT_THRESHOLD < maxIntensity < HIGH_FAT_THRESHOLD, at least two subsequent points are within fat - a sign for flat plateau |
| II (e.g., FIGS. 12C and 12D) | maxIntensity > HIGH_FAT_THRESHOLD |
| III (e.g., FIG. 12B) | LOW_FAT_THRESHOLD < maxIntensity < HIGH_FAT_THRESHOLD, no flat plateau observed |
| IV (e.g., FIG. 13B and 13C) | INNER_WALL_THRESHOLD < maxIntensity < LOW_FAT_THRESHOLD |
| V (e.g., FIG. 13A) | maxIntensity < INNER_WALL_THRESHOLD |

In FIGS. 12 and 13, C2=LesionCntr2X,Y,Z ($2^{nd}$ centroid) and WT2=WallThick2. Zero on horizontal axes corresponds to LesionCentroidX,Y,Z ($1^{st}$ centroid) while intensity profile (vertical axes) is shown along ray=NormalX,Y,Z. Point corresponding to maxIntensity has (e.g., always) positive x coordinate (although ultimate max found along ray may be found higher for negative x coordinate—see e.g. FIG. 12D "indirect case").

Details of Exemplary Implementation: Classifier

As described above, the classifier can be chosen from a variety of architectures and include any combination of the described characteristics. For example, a classifier can be built as a neural network and trained on neck characteristics, normalized wall thickness, and template matching measurements. After training, the neural network can be tested and then deployed for use.

Details of Exemplary Implementation: Presenting Results

Figure 19:
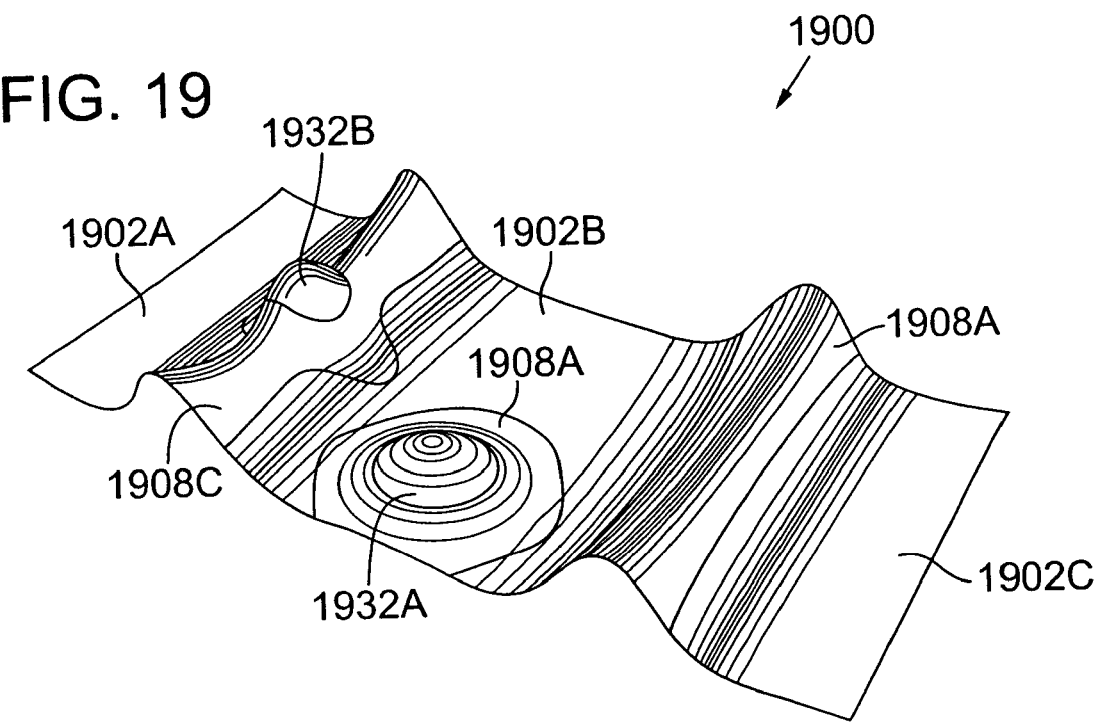
FIG. 19 is a view of a graphical depiction presented for identification of anomalies of interest.

FIG. 19 shows an exemplary graphical depiction 1900 of a portion of a virtual anatomical structure. In a presented user interface that can be used in conjunction with any of the technologies described herein, the depiction 1900 includes colored areas (e.g., regions) to assist in detection of anomalies of interest (e.g., polyps).

In the example depiction 1900, areas 1902A, 1902B, and 1902C can appear in a first color (e.g., yellow) to denote regions of elliptical curvature of the pit subtype. The areas 1908A, 1908B, and 1908C can appear in a second color (e.g., green) to denote regions of hyperbolic curvature (e.g., possible necks of anomalies). The areas 1932A and 1932B can appear in a third color (e.g., orange) to indicate elliptical curvature of the peak subtype (e.g., likely anomaly sites).

Exemplary Computer System for Conducting Analysis

Figure 20:
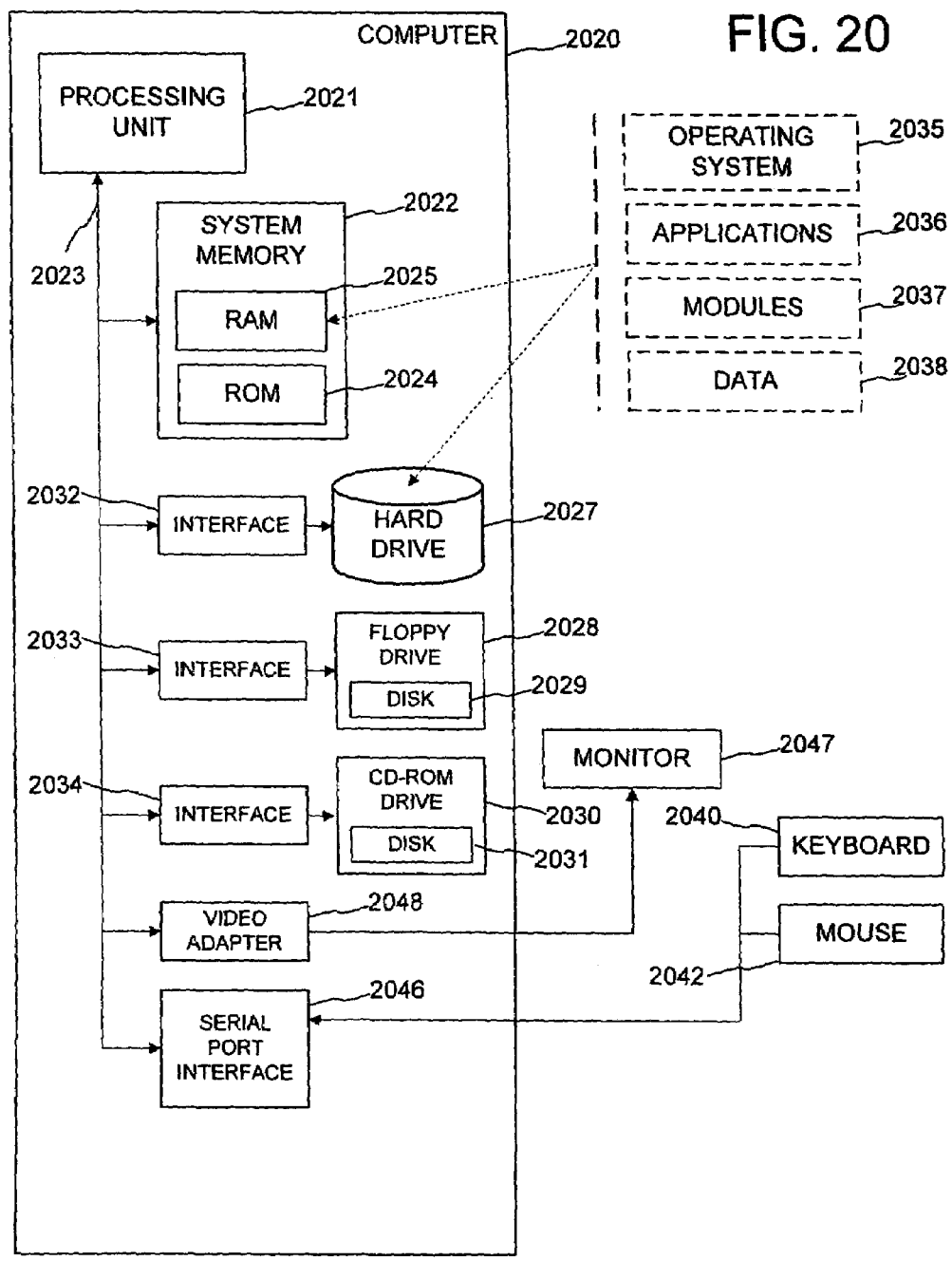
FIG. 20 is a block diagram of an exemplary computer system for implementing the described technologies.

FIG. 20 and the following discussion provide a brief, general description of a suitable computing environment for the software (e.g., computer programs) described above. The methods described above can be implemented in computer-executable instructions organized in program modules. The program modules include the routines, programs, objects, components, and data structures that perform the tasks and implement the data types for implementing the techniques described above.

While FIG. 20 shows a typical configuration of a desktop computer, the invention may be implemented in other computer system configurations, including multiprocessor systems, microprocessor-based or programmable consumer electronics, minicomputers, mainframe computers, and the like. The invention may also be used in distributed computing environments where tasks are performed in parallel by processing devices to enhance performance. For example, tasks related to measuring characteristics of candidate anomalies can be performed simultaneously on multiple computers, multiple processors in a single computer, or both. In a distributed computing environment, program modules may be located in both local and remote memory storage devices.

The computer system shown in FIG. 20 is suitable for implementing the technologies described herein and includes a computer 2020, with a processing unit 2021, a system memory 2022, and a system bus 2023 that interconnects various system components, including the system memory to the processing unit 2021. The system bus may comprise any of several types of bus structures including a memory bus or memory controller, a peripheral bus, and a local bus using a bus architecture. The system memory includes read only memory (ROM) 2024 and random access memory (RAM) 2025. A nonvolatile system 2026 (e.g., BIOS) can be stored in ROM 2024 and contains the basic routines for transferring information between elements within the personal computer 2020, such as during start-up. The personal computer 2020 can further include a hard disk drive 2027, a magnetic disk drive 2028, e.g., to read from or write to a removable disk 2029, and an optical disk drive 2030, e.g., for reading a CD-ROM disk 2031 or to read from or write to other optical media. The hard disk drive 2027, magnetic disk drive 2028, and optical disk drive 2030 are connected to the system bus 2023 by a hard disk drive interface 2032, a magnetic disk drive interface 2033, and an optical drive interface 2034, respectively. The drives and their associated computer-readable media provide nonvolatile storage of data, data structures, computer-executable instructions (including program code such as dynamic link libraries and executable files), and the like for the personal computer 2020. Although the description of computer-readable media above refers to a hard disk, a removable magnetic disk, and a CD, it can also include other types of media that are readable by a computer, such as magnetic cassettes, flash memory cards, digital video disks, and the like.

A number of program modules may be stored in the drives and RAM 2025, including an operating system 2035, one or more application programs 2036, other program modules 2037, and program data 2038. A user may enter commands and information into the personal computer 2020 through a keyboard 2040 and pointing device, such as a mouse 2042. Other input devices (not shown) may include a microphone, joystick, game pad, satellite dish, scanner, or the like. These and other input devices are often connected to the processing unit 2021 through a serial port interface 2046 that is coupled to the system bus, but may be connected by other interfaces, such as a parallel port, game port, or a universal serial bus (USB). A monitor 2047 or other type of display device is also connected to the system bus 2023 via an interface, such as a display controller or video adapter 2048. In addition to the monitor, personal computers typically include other peripheral output devices (not shown), such as speakers and printers.

The above computer system is provided merely as an example. The technologies can be implemented in a wide variety of other configurations. Further, a wide variety of approaches for collecting and analyzing data related to processing candidate anomalies is possible. For example, the data can be collected, characteristics measured, anomalies classified, and the results presented on different computer systems as appropriate. In addition, various software aspects can be implemented in hardware, and vice versa.

Alternatives

Having illustrated and described the principles of the invention in exemplary embodiments, it should be apparent to those skilled in the art that the described examples are illustrative embodiments and can be modified in arrangement and detail without departing from such principles.

Although some of the examples describe colonography and detecting polyps in a virtual colon, the technologies can be applied to other anatomical structures as well. For example implementations can be applied to the bronchus, blood vessels, bladder, urinary tract, billiary tract, cerebrospinal spinal fluid containing spaces of the brain, paranasal sinuses, chambers of the heart, and the like.

In any of the methods described herein, processing can be performed by software in an automated system without intervention by a user. However, user intervention may be desired in some cases, such as to adjust parameters or consider results.

In view of the many possible embodiments to which the principles of the invention may be applied, it should be understood that the illustrative embodiments are intended to teach these principles and are not intended to be a limitation on the scope of the invention. We therefore claim as our invention all that comes within the scope and spirit of the following claims and their equivalents.

We claim:

1. A computer-implemented method for processing a detected anomaly in an anatomical structure, the method comprising:

in a digital representation comprising a representation of the anomaly, measuring a characteristic of a neck of the anomaly; and based at least on the characteristic of the anomaly neck, classifying the anomaly.

2. A computer-readable medium comprising computer-executable instructions for performing the method of claim 1.

3. The method of claim 1 wherein classifying comprises disqualifying the anomaly from being of interest.

4. The method of claim 1 wherein classifying comprises designating the anomaly as being of interest.

5. The method of claim 1 wherein the candidate anomaly comprises a surface anomaly.

6. The method of claim 1 wherein the candidate anomaly comprises a wall surface anomaly.

7. Performing the method of claim 1 for a plurality of candidate anomalies.

8. The method of claim 7 wherein the candidate anomalies are discovered via measured curvatures associated with regions in the digital representation.

9. The method of claim 1 wherein:
the anatomical structure comprises a colon; and
classifying the anomaly comprises designating the anomaly as a polyp.

10. The method of claim 1 wherein:
the anatomical structure comprises a bronchus; and
classifying the anomaly comprises designating the anomaly as a lesion.

11. The method of claim 1 wherein the characteristic comprises neck size.

12. The method of claim 1 wherein the characteristic comprises neck height.

13. The method of claim 1 wherein the characteristic comprises neck circumference.

14. The method of claim 1 wherein the characteristic comprises area enclosed by the neck.

15. The method of claim 1 wherein the characteristic comprises neck angle.

16. The method of claim 1 wherein the characteristic comprises orientation of the neck.

17. The method of claim 1 wherein the characteristic comprises irregularity of the neck.

18. The method of claim 17 wherein irregularity comprises jaggedness of the neck.

19. The method of claim 17 wherein irregularity of the neck is determined via a fractal technique.

20. The method of claim 1 wherein the characteristic comprises curvature of the neck.

21. The method of claim 20 wherein the curvature comprises Gaussian curvature.

22. The method of claim 20 wherein the curvature comprises mean curvature.

23. The method of claim 20 wherein the curvature comprises principal curvature.

24. The method of claim 23 wherein the curvature comprises maximum principal curvature.

25. The method of claim 23 wherein the curvature comprises minimum principal curvature.

26. The method of claim 20 wherein the curvature comprises shape index.

27. The method of claim 20 wherein the curvature comprises curvedness.

28. The method of claim 20 wherein the curvature is calculated via partial derivatives.

29. The method of claim 20 wherein the curvature is calculated via finite differences.

30. The method of claim 20 wherein the curvature is calculated via convolution kernels.

31. The method of claim 20 wherein the curvature is calculated via fitting approximating curves.

32. The method of claim 20 wherein the curvature is calculated via fitting approximating surfaces.

33. The method of claim 1 wherein the characteristic comprises relation of the neck to adjacent haustral folds.

34. The method of claim 1 further comprising:
fitting a plane to the circumference of the neck;
measuring protrusion of the anomaly; and
based also at least on the characteristic of the anomaly neck, classifying the anomaly.

35. The method of claim 1 further comprising:
identifying an edge in the representation of the anomaly and an adjacent wall of the representation of the anatomical structure;
wherein the characteristic comprises an angle made by a junction of the anomaly with the wall.

36. The method of claim 35 wherein the edge is identified via segmenting.

37. The method of claim 35 wherein the edge is identified via an isosurface technique.

38. The method of claim 35 wherein the edge is identified via a level set technique.

39. A computer-implemented method for processing a detected candidate polyp in a virtual colon, the method comprising:
via the virtual colon, measuring a characteristic of a neck of the detected candidate polyp; and
based at least on the characteristic of the neck, classifying the candidate polyp.

40. A computer-implemented method for processing an anomaly in an anatomical structure, the method comprising:
in a digital representation of the anatomical structure comprising a representation of the anomaly, identifying a neck of the anomaly;
based at least on the anomaly neck, measuring protrusion of the anomaly; and
based at least on the protrusion of the anomaly, classifying the anomaly.

41. The method of claim 40 wherein measuring protrusion comprises fitting a plane to the circumference of the neck.

42. A computer-generated user interface for presenting a graphical representation of an anatomical structure, the user interface comprising:
a depiction of the anatomical structure;
wherein regions of the anatomical structure having a curvature indicative of an anomaly neck are depicted specially.

43. The computer-generated usrer interface of claim 42 wherein regions of the anatomical structure having a curvature indicitave of an in a distinctive color.

44. The computer-generated user interface of claim 43 wherein the curvature indicative of an anomaly neck comprises hyperbolic curvature.

* * * * *

UNITED STATES PATENT AND TRADEMARK OFFICE
CERTIFICATE OF CORRECTION

| | | |
|---|---|---|
| PATENT NO. | : 7,260,250 B2 | Page 1 of 1 |
| APPLICATION NO. | : 10/671749 | |
| DATED | : August 21, 2007 | |
| INVENTOR(S) | : Summers et al. | |

It is certified that error appears in the above-identified patent and that said Letters Patent is hereby corrected as shown below:

<u>In the Claims:</u>

Column 26, line 24, "of an in a distinctive color" should read -- of an anomaly neck are depicted in a distinctive color --

Signed and Sealed this

Second Day of December, 2008

JON W. DUDAS
*Director of the United States Patent and Trademark Office*